(12) United States Patent
Arkoff et al.

(10) Patent No.: US 12,337,143 B1
(45) Date of Patent: Jun. 24, 2025

(54) SMART IV POLE: AN INTEGRATED SOLUTION FOR MEDICAL DEVICE CONNECTIVITY, PATIENT MONITORING, AND COMMUNICATION

(71) Applicant: OneSource Solutions International, Inc., Sudbury, MA (US)

(72) Inventors: Harold Arkoff, Sudbury, MA (US); Vedran Jukic, Trieste (IT)

(73) Assignee: OneSource Solutions International, Inc., Sudbury, MA (US)

( * ) Notice: Subject to any disclaimer, the term of this patent is extended or adjusted under 35 U.S.C. 154(b) by 0 days.

(21) Appl. No.: 19/000,461

(22) Filed: Dec. 23, 2024

Related U.S. Application Data

(60) Provisional application No. 63/689,694, filed on Aug. 31, 2024.

(51) Int. Cl.
*A61M 5/172* (2006.01)
*A61M 5/14* (2006.01)
*G16H 10/60* (2018.01)
*G16H 40/20* (2018.01)
*G16H 40/67* (2018.01)

(52) U.S. Cl.
CPC ........ *A61M 5/1723* (2013.01); *A61M 5/1415* (2013.01); *G16H 10/60* (2018.01); *G16H 40/20* (2018.01); *G16H 40/67* (2018.01); *A61M 2205/18* (2013.01); *A61M 2205/3306* (2013.01); *A61M 2205/3334* (2013.01); *A61M 2205/3592* (2013.01); *A61M 2205/584* (2013.01); *A61M 2230/63* (2013.01)

(58) Field of Classification Search
CPC .................................................. A61M 5/1723
See application file for complete search history.

(56) References Cited

U.S. PATENT DOCUMENTS

| 6,348,777 B1 * | 2/2002 | Brown | H02J 7/007194 |
| | | | 320/160 |
| 2006/0065713 A1 * | 3/2006 | Kingery | G16H 20/13 |
| | | | 235/380 |
| 2007/0135779 A1 * | 6/2007 | Lalomia | A61M 1/63 |
| | | | 604/319 |

(Continued)

*Primary Examiner* — Manuel A Mendez
(74) *Attorney, Agent, or Firm* — IP CONSULTING GROUP; Michael Razavi; Alfred F Hoyte, Jr.

(57) ABSTRACT

A smart intravenous (IV) pole is disclosed, designed to maintain communications and seamlessly integrate medical devices even as a patient is relocated. The IV pole includes at least one antenna, and a network interface adapted for seamless communication during patient movement. The IV pole also includes a circuitry configured to obtain patient data associated with a patient. The IV pole retrieves one or more electronic medical health records associated with the patient. The IV pole retrieves medical data associated with the patient. The IV pole applies artificial intelligence (AI) models to at least one of the patient data, the electronic medical health records, or the medical data. The IV pole generates alerts associated with a medical condition of the patient and renders the alerts. The IV pole ensures uninterrupted data connectivity, monitoring, and communication during and after relocation, enhancing patient safety and supporting dynamic clinical workflows in modern healthcare environments.

20 Claims, 6 Drawing Sheets

(56) References Cited

U.S. PATENT DOCUMENTS

| | | | |
|---|---|---|---|
| 2007/0159772 A1* | 7/2007 | Morice | H01R 13/60 361/600 |
| 2009/0112630 A1* | 4/2009 | Collins, Jr. | H04L 67/125 705/2 |
| 2014/0148104 A1* | 5/2014 | Marterstock | A61B 90/90 455/73 |
| 2014/0171770 A1* | 6/2014 | Hann | A61B 5/0205 604/510 |
| 2017/0117931 A1* | 4/2017 | Concepcion | H04B 1/40 |
| 2021/0398650 A1* | 12/2021 | Baker | G16H 80/00 |
| 2022/0277843 A1* | 9/2022 | Koker | G16H 30/40 |
| 2023/0245771 A1* | 8/2023 | Wang | G16H 15/00 705/2 |
| 2024/0079128 A1* | 3/2024 | Chen | G16H 50/20 |
| 2024/0371522 A1* | 11/2024 | Joseph | G16H 50/20 |

* cited by examiner

SMART IV POLE: AN INTEGRATED SOLUTION FOR MEDICAL DEVICE CONNECTIVITY, PATIENT MONITORING, AND COMMUNICATION

FIELD OF TECHNOLOGY

The present disclosure relates generally to medical devices, and more specifically to a multifunctional smart intravenous pole designed for clinical communication and medical device integration infrastructure, even during rapid patient relocation.

BACKGROUND

Traditionally, the intravenous (IV) pole has served a basic and largely passive function within healthcare settings. Its primary purpose has been to provide support for intravenous fluid bags, nutrition sources, and, occasionally, medical devices such as infusion pumps, syringes, or medication delivery systems. The IV pole's design typically consists of a vertical, adjustable structure with one or more hooks or arms for hanging fluid bags and devices, along with casters for mobility. Historically, this design has remained relatively unchanged for decades, with little evolution in terms of functionality, beyond modest adjustments to height or weight capacity.

While the traditional IV pole includes casters for movement, it lacks the integration necessary to facilitate quick and reliable relocation of medical devices and communication infrastructure. The IV pole, in its traditional form, has primarily been a physical tool with minimal integration into the broader network of healthcare technologies. While the pole is essential for maintaining intravenous access to patients, it remains a passive item in the overall care process. Traditionally, the responsibility of managing and monitoring the IV flow, medication delivery, and patient response has fallen on healthcare providers who manually monitor these parameters using separate, standalone devices. As a result, medical professionals must often track numerous variables across multiple systems, leading to potential inefficiencies, increased cognitive load, and a heightened risk for errors. This fragmentation becomes particularly problematic during patient relocation, where multiple devices must be disconnected and reconnected, increasing the risk of errors and delays.

However, with the rapid advancement of medical technologies and the increasing emphasis on patient-centric care, healthcare environments have evolved significantly. The proliferation of integrated communication, monitoring, and data management systems has reshaped many aspects of patient care. In particular, hospitals and healthcare facilities have seen a growing need for more sophisticated and automated solutions that can streamline operations, improve patient outcomes, and reduce the risk of medical errors-especially during patient transfers and emergency situations.

Despite these advancements, the conventional IV pole has remained relatively underutilized in this context. It has largely been seen as a standalone object, with limited functionality beyond its traditional role of supporting fluid bags. This gap has become more pronounced as medical devices-such as infusion pumps, electronic health record (EHR) systems, remote patient monitoring tools, and other connected devices—have increasingly become integral to patient care. The lack of a reliable, mobile platform to integrate these technologies hampers the ability to provide continuous care during patient movement. While these devices collect valuable data, the lack of connectivity and integration within the traditional IV pole setup has resulted in missed opportunities to improve workflow, patient safety, and clinical decision-making.

For example, in modern healthcare environments, a nurse or clinician might need to manage several IV poles in a single patient room, each connected to a different infusion device, pump, or monitoring equipment. During an emergency transfer, each of these devices may require separate handling, increasing the time and complexity of relocation. Each of these devices may require separate inputs, manual oversight, and individual monitoring, often on different platforms or interfaces. This fragmentation creates an environment ripe for inefficiency and error, as healthcare workers must divide their attention across numerous systems while simultaneously managing the human aspects of patient care and ensuring patient safety during movement. Additionally, physical interactions with these devices, such as adjusting infusion rates, replacing fluid bags, or troubleshooting alarms, require time and focus, leading to potential delays in timely interventions.

Moreover, the integration of electronic health records (EHR), remote monitoring systems, and other healthcare technologies often remain disconnected from the IV pole itself. There is no seamless connection between the IV pole and the patient's broader health monitoring systems, especially during relocation. For instance, while IV fluids and medications may be tracked manually or on paper by clinicians, there is no seamless connection between the IV pole and the patient's broader health monitoring systems. This disconnection creates challenges in ensuring that data related to medication administration, infusion rates, and patient responses are recorded accurately and in real-time, particularly during transfers. In turn, this can result in incomplete data tracking, which impairs clinical decision-making and contributes to inefficiencies in the workflow.

As healthcare continues to evolve, there is a growing recognition of the need for more integrated, mobile, data-driven solutions that can optimize the delivery of care. The demand for smarter, more connected healthcare devices is increasing, with a particular focus on devices that can actively communicate with other medical equipment, provide real-time monitoring, and offer predictive insights to support clinical decision-making-even during patient relocation. The potential to leverage the IV pole as a more dynamic tool—one capable of contributing to real-time data collection, patient monitoring, and communication within a larger health ecosystem, particularly during movement—has not yet been fully realized.

There is, therefore, a significant opportunity to enhance the functionality of the traditional IV pole by incorporating advanced technologies such as sensors, wireless communication capabilities, and smart data processing, all designed to support rapid patient relocation. By transforming the IV pole from a passive support structure into an intelligent, mobile, interactive hub, it can become an integral part of the broader healthcare infrastructure. A smart IV pole could support integrated data collection from various connected medical devices, monitor patient vitals and fluid intake, issue alerts or alarms to clinicians based on specific parameters, and even automate certain aspects of patient care such as fluid administration.

Hospitals and other healthcare facilities needs to be updated continually and displayed immediately to attending medical personnel, without interruption due to relocation. Patient data collected during operations, medical procedures, and patient recovery needs to be updated continually and displayed immediately to attending medical personnel, without interruption due to relocation. The patient data is permanently retained in a standard format useful for facility management and medical researchers among others who may be in remote locations and/or need to compare data from myriad healthcare facilities.

In typical hospital settings such as an operating room, ICU, recovery room, etc., there are multiple medical devices surrounding a patient. In some scenarios, medical data received from one device has to be shared with other devices so that the output can be generated. However, such sharing of medical data between medical devices is complicated and cumbersome because of the different protocols used by the medical devices. This complexity is exacerbated during patient transfers, new relocation of patient care, where maintaining seamless connectivity is critical.

The present disclosure provides a technical solution to the long-standing problem of integrating heterogeneous medical devices in dynamic healthcare environments. Unlike prior art systems, which are limited to device-specific data collection, the present disclosure utilizes a multifunctional intravenous (IV) pole equipped with specialized hardware components, including a retractable antenna, advanced sensors, and integrated AI models, to dynamically process, analyze, and transmit medical data in real-time. The present disclosure is designed to reduce electromagnetic interference in crowded healthcare settings and ensure uninterrupted data flow for critical care.

The AI models implemented within the IV pole are embedded directly into the pole's circuitry, leveraging the hardware's processing capabilities to enable real-time analysis of patient data. For example, convolutional neural networks (CNNs) process wound images captured by the integrated image sensor, while recurrent neural networks (RNNs) analyze accelerometer and gyroscopic data to predict fall risks. These models are trained on diverse medical datasets, ensuring their accuracy and reliability for clinical applications.

In a mass casualty event, the IV pole's retractable antenna and LoRa connectivity enable seamless monitoring and triage of multiple patients over extended ranges, providing real-time alerts to medical personnel. This practical application demonstrates the invention's ability to address critical real-world challenges.

BRIEF SUMMARY OF THE DISCLOSURE

Systems and/or methods are provided for data transfer mechanisms between medical devices for medical data governance, substantially as shown in and/or described in connection with at least one of the figures, as set forth more completely in the claims.

According to an embodiment of the disclosure, an IV pole includes at least one antenna designed to maintain uninterrupted data connectivity during movement and a network interface adapted for seamless communication across different network environments during at least one of a movement of the IV pole or a relocation of a patient. Furthermore, the IV pole includes circuitry configured to obtain, from one or more data sources, patient data associated with a patient, ensuring continuous data acquisition during at least one of the movement of the IV pole or the relocation of the patient. The circuitry is further configured to retrieve one or more electronic medical health records associated with the patient based on the obtained patient data, without interruption due to at least one of a movement of the IV pole or a relocation of the patient. It retrieves, from one or more medical databases, medical data associated with the patient based on a correlation of the patient data with the electronic medical health records. The circuitry applies one or more artificial intelligence (AI) models to the patient data, electronic medical health records, or medical data. It generates one or more alerts associated with a medical condition of the patient based on the AI models, maintaining alert functionality during at least one of the movement of the IV pole or the relocation of the patient and renders the generated alerts, ensuring accessibility during at least one of the movement of the IV pole or the relocation of the patient.

Critically, the IV pole is designed to support dynamic clinical workflows by ensuring that all integrated medical devices, monitoring systems, and communication interfaces remain fully operational during relocation. Whether in emergency care settings, ICU transfers, or mass casualty situations, the IV pole's mobility and infrastructure dependability ensure that patient care is not compromised during movement.

According to an embodiment of the disclosure, the one or more data sources comprise at least one of a set of diagnostic medical devices associated with the patient, a set of monitoring devices associated with the patient, a set of scanning devices associated with the patient, a set of wearable devices associated with the patient, a set of fluid administration devices associated with the patient, and a set of sensors, and wherein the one or more data sources are associated with the IV pole.

According to an embodiment of the disclosure, the circuitry is further configured to encrypt the patient data, the one or more electronic medical health records, or the one or more alerts. The one or more electronic medical health records, or the one or more alerts are encrypted using one or more encryption techniques. The circuitry is further configured to transmit, via the network interface, the encrypted patient data, the encrypted one or more electronic medical health records, or the encrypted one or more alerts to at least one electronic device of a set of electronic devices.

According to an embodiment of the disclosure, the circuitry is further configured to receive a set of instructions associated with the administration of one or more fluids to the patient based on the transmission. The circuitry is further configured to control the flow rate of the one or more fluids to the patient based on the received set of instructions.

According to an embodiment of the disclosure, the one or more encryption techniques include at least one of an Advanced Encryption Standard (AES) technique, a Data Encryption Standard (DES) technique, a Triple Data Encryption Standard (3DES) technique, a Rivest-Shamir-Adleman (RSA) technique, an Elliptic Curve Cryptography (ECC) technique, and a Blowfish (BF) technique.

According to an embodiment of the disclosure, the circuitry is further configured to obtain location data associated with the location of at least one user device of a set of user devices associated with a set of medical professionals. The circuitry is further configured to generate a set of navigation instructions based on the obtained location data to facilitate efficient coordination during at least one of the movement of the IV pole or the relocation of the patient. The circuitry is further configured to transmit the generated navigation instructions to the at least one user device of the set of user devices.

According to an embodiment of the disclosure, the IV pole includes an image capture sensor and the circuitry is further configured to control the image capture sensor to capture an image of a wound of the patient. The patient data includes the captured image. The circuitry is further configured to apply a first AI model of the one or more AI models on the captured image. The circuitry is further configured to generate the one or more alerts associated with the medical condition of the patient based on the application of the first AI model on the captured image.

According to an embodiment of the disclosure, the circuitry is further configured to obtain, from the one or more data sources, the patient data associated with the patient. The one or more data sources include at least one of a set of wearable devices associated with the patient and a set of sensors. The circuitry is further configured to apply a second AI model of the one or more AI models on the obtained patient data. The patient data include at least one of accelerometer data associated with a movement of the patient, or gyroscopic data associated with the movement of the patient. The circuitry is further configured to generate the one or more alerts associated with the medical condition of the patient based on the application of the second AI model on the obtained patient data, monitoring patient stability during at least one of the movement of the IV pole or the relocation of the patient.

According to an embodiment of the disclosure, the circuitry is further configured to apply a third AI model of the one or more AI models on the obtained patient data. The circuitry is further configured to generate the one or more alerts associated with the medical condition of the patient based on the application of the third AI model on the obtained patient data. The one or more alerts are indicative of a repositioning of the patient to prevent one or more pressure sores associated with the patient, even during at least one of the movement of the IV pole or the relocation of the patient.

According to an embodiment of the disclosure, the IV pole is connected with one or more display devices using a customized active cable arrangement designed to maintain connectivity during at least one of the movement of the IV pole or the relocation of the patient.

According to an embodiment of the disclosure, the circuitry is further configured to receive a first user input associated with retraction of the at least one antenna, and control the at least one antenna to retract inside the IV pole based on the received first user input.

According to an embodiment of the disclosure, the IV pole includes a set of visual indicators, and the circuitry is configured to control a display of a first color in a first visual indicator of the set of visual indicators based on the patient data.

According to an embodiment of the disclosure, a method implemented in an intravenous (IV) pole including at least one antenna and a network interface is described. The method includes obtaining, from one or more data sources, patient data associated with a patient. The method includes retrieving one or more electronic medical health records associated with the patient based on the obtained patient data. The method includes retrieving, from one or more medical databases, medical data associated with the patient based on a correlation of the patient data with the one or more electronic medical health records. The method includes applying one or more artificial intelligence (AI) models to at least one of the patient data, the electronic medical health records, or the medical data. The method includes generating one or more alerts associated with a medical condition of the patient based on the application of the one or more AI models t to at least one of the patient data, the electronic medical health records, or the medical data. The method includes rendering the generated one or more alerts.

According to an embodiment of the disclosure, the one or more data sources include at least one of a set of diagnostic medical devices associated with the patient, a set of monitoring devices associated with the patient, a set of scanning devices associated with the patient, a set of wearable devices associated with the patient, a set of fluid administration devices associated with the patient, and a set of sensors.

According to an embodiment of the disclosure, the method further includes encrypting the patient data, the one or more electronic medical health records, or the one or more alerts. The one or more electronic medical health records, or the one or more alerts are encrypted using one or more encryption techniques. The method further includes transmitting, via the network interface, the encrypted patient data, the encrypted one or more electronic medical health records, or the encrypted one or more alerts to at least one electronic device of a set of electronic devices.

According to an embodiment of the disclosure, the method further includes receiving a set of instructions associated with an administration of one or more fluids to the patient based on the transmission and controlling a flow rate of the one or more fluids to the patient based on the received set of instructions.

According to an embodiment of the disclosure, the method further includes obtaining location data associated with a location of at least one user device of a set of user devices associated with a set of medical professionals. The method further includes generating a set of navigation instructions based on the obtained location data and transmitting the generated navigation instructions to the at least one user device of the set of user devices.

According to an embodiment of the disclosure, the method further includes controlling an image capture sensor to capture an image of a wound of the patient. The patient data includes the captured image. The method further includes applying a first AI model of the one or more AI models on the captured image and generating the one or more alerts associated with the medical condition of the patient based on the application of the first AI model on the captured image.

According to an embodiment of the disclosure, the method further includes obtaining, from the one or more data sources, the patient data associated with the patient. The one or more data sources include at least one of a set of wearable devices associated with the patient and a set of sensors. The method further includes applying a second AI model of the one or more AI models on the obtained patient data. The patient data includes at least one of accelerometer data associated with a movement of the patient, or gyroscopic data associated with the movement of the patient. The method further includes generating the one or more alerts associated with the medical condition of the patient based on the application of the second AI model on the obtained patient data.

According to an embodiment of the disclosure a non-transitory computer-readable medium including computer program instructions is disclosed. The non-transitory computer-readable medium including computer program instructions when executed by an intravenous (IV) pole including at least one antenna, and a network interface, cause the IV pole to perform one or more operations including obtaining, from one or more data sources, patient data associated with a patient. The one or more operations include retrieving one or more electronic medical health records associated with the patient based on the obtained patient data. The one or more operations include retrieving, from one or more medical databases, medical data associated with the patient based on a correlation of the patient data with the one or more electronic medical health records. The one or more operations include applying one or more artificial intelligence (AI) models to at least one of the patient data, the electronic medical health records, or the medical data. The one or more operations include generating one or more alerts associated with a medical condition of the patient based on the application of the one or more AI models to at least one of the patient data, the electronic medical health records, or the medical data. The one or more operations include rendering the generated one or more alerts.

Therefore, the disclosed IV pole reimagines the traditional IV poles as an active, dynamic, and mobile element within the patient care ecosystem. The disclosure transforms the IV pole into a central hub for communication, monitoring, and device management, seamlessly integrating with modern healthcare technologies even during patient transfers. By incorporating wireless communication modules, sensors, and AI-driven systems, the disclosed IV pole facilitates continuous data transfer between connected devices, patient monitoring systems, and healthcare management platforms during and after relocation. This centralized communication reduces the need for manual data entry, ensuring that healthcare providers have access to real-time, accurate patient information at all times, thus improving clinical decision-making and reducing the risk of errors.

With the ability to maintain uninterrupted connectivity, monitor critical patient parameters such as heart rate, oxygen levels, and fluid intake, the disclosed IV pole enhances patient safety by ensuring continuous monitoring and data availability, even during transfers. The system's AI-driven predictive capabilities further enhance safety by identifying early signs of complications, such as fluid overload or sepsis, allowing healthcare providers to take preventive action before conditions escalate. These predictive insights can significantly improve patient outcomes by enabling a more proactive, data-driven approach to care.

Furthermore, by consolidating various medical devices, such as infusion pumps, cameras, and sensors, into a single, mobile platform, the disclosed IV pole optimizes clinical workflows. It minimizes the need for separate devices and interfaces, reducing cognitive load on healthcare staff, including and during patient movement. Now, nurses and clinicians can remotely monitor patients, adjust infusion rates, and receive instant alerts directly from the disclosed IV pole, which streamlines care delivery and reduces response times even in transit. The integration of the disclosed IV pole with electronic health records (EHR) systems ensures that patient data such as medication administration, infusion rates, and vital signs are automatically updated in real-time, eliminating the need for manual documentation and reducing the risk of data entry errors.

The disclosed IV pole also optimizes space within patient rooms, organizing and managing essential medical equipment in a centralized, mobile manner. By housing infusion pumps, monitoring devices, cameras, and antennas, the disclosed IV pole reduces clutter, frees up valuable room space and makes it easier for healthcare providers to access necessary equipment without disruption. The mobility and flexibility of the IV pole ensure that the IV pole can be easily moved within the patient room or across different care areas, maintaining the same level of accessibility and functionality while allowing providers to monitor and care for patients effectively, even during new relocation or transition Beyond the immediate clinical environment, the disclosed IV pole also supports remote care capabilities. Through telemedicine integration, the disclosed IV pole can securely transmit patient data to healthcare providers, enabling remote monitoring and consultations without interruption. This is particularly valuable in remote or underserved areas, allowing specialists to review patient data and collaborate with on-site caregivers without needing to be physically present. The ability of the disclosed IV pole to automatically synchronize data with EHR systems and send alerts directly to healthcare providers ensures that all members of the care team are informed in real-time, facilitating better coordination and collaboration, which in turn improves overall patient care.

In addition to its clinical advantages, the disclosed IV pole enhances patient experience by ensuring timely interventions and more comprehensive monitoring. By housing the necessary medical devices and leveraging AI-driven insights, it allows for more accurate and responsive care, resulting in better patient outcomes and faster recovery times. The visual and functional integration of the disclosed IV pole within the patient room also contributes to a more organized, reassuring, and efficient care environment, giving patients confidence that their condition is actively monitored and managed with cutting-edge technology, even during transfers. Ultimately, the disclosed IV pole transforms a traditionally passive medical device into a powerful, integrated tool that enhances patient care, improves workflow and supports more personalized, data-driven healthcare delivery at any location.

Therefore, the disclosure discloses a versatile and universal medical device support system centered around the IV pole that can be integrated into various patient care platforms, including stretchers, gurneys, wheelchairs, waiting area chairs, and triage stretchers facilitating rapid relocation of clinical communication and medical device integration infrastructure. The IV pole is designed with a custom base system where each base is tailored to fit specific manufacturers' equipment while the pole itself remains universally attachable to any base. The pole can be either fixed length or collapsible, offering flexibility in various medical environments.

The innovation of this disclosure lies in transforming the IV pole from a passive support structure into an active, mobile, multifunctional device that integrates advanced communication technologies and medical monitoring systems. The IV pole is no longer just for holding IV fluid bags; it has become a dynamic element that supports wireless communication, AI-driven monitoring, and real-time data management.

DETAILED DESCRIPTION OF THE DISCLOSURE

Various aspects of the disclosure may be found in a system and method for data transfer mechanism between medical devices for medical data governance supporting quick and reliable relocation of clinical communication and medical device integration infrastructure.

Figure 1:
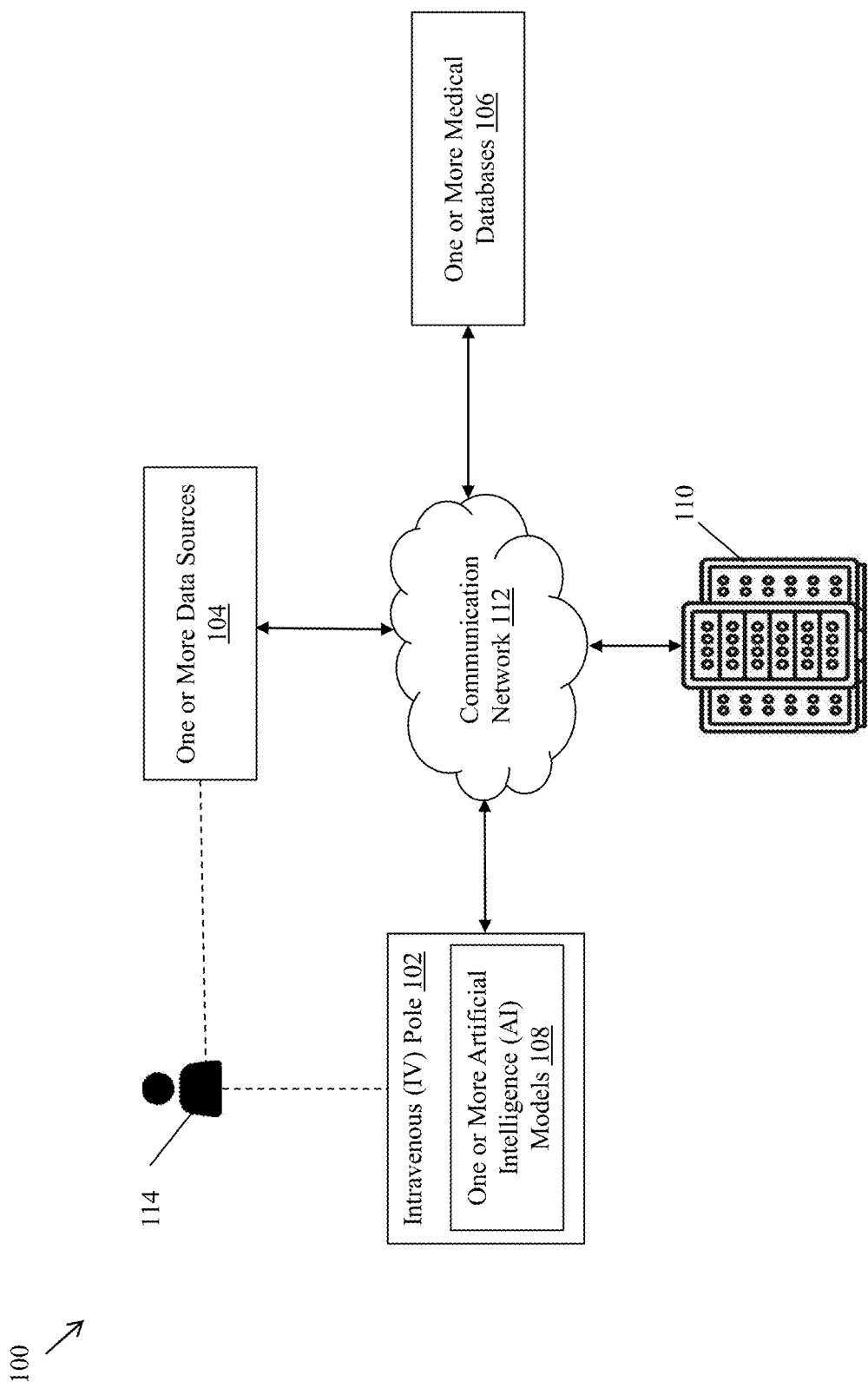
FIG. 1 is a block diagram that illustrates an exemplary environment for the generation of alerts by an intravenous pole, in accordance with an exemplary embodiment of the disclosure.

FIG. 1 is a block diagram that illustrates an exemplary environment for the generation of alerts by an intravenous pole, in accordance with an exemplary embodiment of the disclosure. Referring to FIG. 1, there is shown a network environment 100, which may include an intravenous (IV) pole 102, one or more data sources 104, one or more medical databases 106 (or one or more medical databases medical data governance (MDG) databases), one or more artificial intelligence (AI) models 108, a server 110, and a communication network 112. The one or more medical databases 106 may include a first medical database 106A, a second medical database 106B, up to an Nth medical database 106N. With reference to FIG. 1, there is further shown a patient 114.

The IV pole 102 may comprise suitable logic, circuitry, interfaces, and/or code that may be configured to obtain, from the one or more data sources 104, patient data associated with the patient 114 and maintain uninterrupted connectivity during patient movement. The IV pole 102 is further configured to retrieve one or more electronic medical health records associated with the patient based on the obtained patient data. The IV pole 102 is further configured to retrieve, from the one or more medical databases 106, medical data associated with the patient 114 based on a correlation of the patient data with the one or more electronic medical health records. The IV pole 102 is further configured to apply the one or more AI models 108 to at least one of the patient data, the electronic medical health records, or the medical data. The IV pole 102 is further configured to generate one or more alerts associated with a medical condition of the patient based on the application of the one or more AI models 108 to at least one of the patient data, the electronic medical health records, or the medical data. The IV pole 102 is further configured to render the generated one or more alerts and ensure that these functionalities are sustained during and after relocation.

In an embodiment, the IV pole 102 may enable medical data governance (MDG) with a focus on mobility and continuous data integrity during and after patient transfers. The MDG may provide a true source of data that can highlight the schedule of medical treatments and provides tools for rescheduling feedback, contacting and receiving feedback from patients/physicians/healthcare professionals thus introducing general system flexibility through the use of lean process and six sigma methods. MDG leverages modern communication methods (phone apps, emails, web services, etc.) and easily links patient's physicians, or other healthcare professionals to the scheduled use of medical devices. After unexpected events that may cause a miss in scheduled operations, the MDG may create a backup schedule to pre-emptively fill the gaps and may facilitate healthcare and schedule professionals to optimize machine time usage. This could create a new marketplace for priority services for those patients who opt for it.

Also, MDG may enable patients/users and or institutions to monetize their vital, medically relevant, patient data collected during the stay inside the healthcare institution, as well through the extended data collected over some time in multiple stays or spot measurements in healthcare institutions. Patients may be able to establish a relationship with a third party (such as a drug manufacturer, independent drug trial projects, undisclosed trials to the institution) and provide to the third party normalized data collected, organized, and provided by the MDG used by the healthcare institution, and provided to the patient in a different standardized format, even in near real-time. The institution might not be aware of the final user of the patient data. MDG can create additional revenue for the institution by charging such a service per patient and data processed. MDG can track and trace data usage per patient and assets. MDG through the export of all specific, validated clinical data, and medical relevant data, could create a new data-based economy.

Furthermore, MDG manages patient consent and approval, or notification for the use of the patient data for second opinions, medical treatments, specific research, validation projects, and educational purposes. Specific patient or user data is previously screened based on always updated, public, generic, anonymous metadata (for example: sex, age, days in hospital, normalized data content and length: heart rate, respiration rate, drugs, etc.). MDG can handle patient consent using modern communication methods (phone apps, emails, web services, etc.) and provide patient consent for his data to be used in a specific research or validation project, with or without compensation. MDG can provide patient consent and access to the data to specific users, like doctors, physicians, and other specific medical professionals. MDG can provide specific code associated with the data, that, based on necessity, can provide, if granted by the user or proxy consent, protected personal identification, family relations, or other protected personal data The MDG may allow for third-party statistical analysis (research) on the whole population dataset, without exporting or providing data to the third party, but rather comparing the result to the legally available consent subset group. A statistically relevant result might indicate a minimal group of statistically significant subset of data to search consent and optimize the time for valid and repeatable datasets.

The IV pole 102 is designed with enhanced mobility features, including robust casters and a stable base, to facilitate rapid relocation within various clinical settings. Its design ensures that all connected devices remain secure and operational during movement, reducing the risk of disconnections or malfunctions.

Each of the one or more data sources 104 may correspond to an originator of medical data (such as the patient data) that may be associated with the patient 114. Each of the one or more data sources 104 may be configured to capture the patient data that may be associated with the patient 114 and further transmit the captured patient data to the IV pole 102 even while in motion. In an embodiment, the one or more data sources 104 may include a set of diagnostic medical devices associated with the patient 114, and a set of scanning devices associated with the patient 114. In an alternate embodiment, the one or more data sources 104 may correspond to databases associated with the set of diagnostic medical devices, and the set of scanning devices. In yet another alternate embodiment, the one or more data sources 104 may correspond to a set of wearable devices associated with the patient 114, a set of fluid administration devices associated with the patient 114, and a set of sensors.

Each of the one or more medical databases 106 may correspond to a structured collection of organized information stored electronically in a way that enables easy access, retrieval, and manipulation of medical data. The one or more medical databases 106 may serve as a centralized database where the medical data may be systematically arranged into tables, records, and fields, following a predefined data model. The one or more medical databases 106 may be designed to efficiently manage vast amounts of information, allowing users to perform queries, insert new data, update existing records, and delete information based on specific requirements. In an embodiment, the one or more medical databases 106 may correspond to a storage system associated with the MDG. Examples of different types of the one or more medical databases 106 may include, but are not limited to, a relational database, a non-relational database, a document database, and a graph database.

Each of the one or more AI models 108 may be a computational network or a system of artificial neurons, arranged in a plurality of layers, as nodes. The plurality of layers of each of the one or more AI models 108 may include an input layer, one or more hidden layers, and an output layer. Each layer of the plurality of layers may include one or more nodes (or artificial neurons). Outputs of all nodes in the input layer may be coupled to at least one node of the hidden layer(s). Similarly, inputs of each hidden layer may be coupled to outputs of at least one node in other layers of each of the one or more AI models 108. Outputs of each hidden layer may be coupled to inputs of at least one node in other layers of each of the one or more AI models 108. Node(s) in the final layer may receive inputs from at least one hidden layer to output a result. The number of layers and the number of nodes in each layer may be determined from hyper-parameters of each of the one or more AI models 108. Such hyper-parameters may be set before or while training each of the one or more AI models 108 on a training dataset.

Each node of each of the one or more AI models 108 may correspond to a mathematical function (e.g., a sigmoid function or a rectified linear unit) with a set of parameters, tunable during training of the network. The set of parameters may include, for example, a weight parameter, a regularization parameter, and the like. Each node may use the mathematical function to compute an output based on one or more inputs from nodes in other layer(s) (e.g., previous layer(s)) of each of the one or more AI models 108. All or some of the nodes of each of the one or more AI models 108 may correspond to the same or a different mathematical function.

In training of each of the one or more AI models 108, one or more parameters of each node of the AI model may be updated based on whether an output of the final layer for a given input (from the training dataset) matches a correct result based on a loss function for each of the one or more AI models 108. The above process may be repeated for the same or a different input until a minima of loss function may be achieved and a training error may be minimized. Several methods for training are known in the art, for example, gradient descent, stochastic gradient descent, batch gradient descent, gradient boost, meta-heuristics, and the like.

Each AI model of the one or more AI models 108 may include electronic data, such as, for example, a software program, code of the software program, libraries, applications, scripts, or other logic or instructions for execution by a processing device, such as circuitry. Each AI model of the one or more AI models 108 may include code and routines configured to enable a computing device, such as the IV pole 102 to perform one or more operations. Additionally, or alternatively, each AI model of the one or more AI models 108 may be implemented using hardware including a processor, a microprocessor (e.g., to perform or control the performance of one or more operations), a field-programmable gate array (FPGA), or an application-specific integrated circuit (ASIC). Alternatively, in some embodiments, each AI model of the one or more AI models 108 may be implemented using a combination of hardware and software. Although in FIG. 1, the one or more AI models 108 is shown integrated within the IV pole 102, the disclosure is not so limited. Accordingly, in some embodiments, the one or more AI models 108 may be a separate entity in the IV pole 102, without deviation from the scope of the disclosure. Examples of each AI model of the one or more AI models 108 may include, but are not limited to, a deep neural network (DNN), a convolutional neural network (CNN), a CNN-recurrent neural network (CNN-RNN), R-CNN, Fast R-CNN, Faster R-CNN, an artificial neural network (ANN), (You Only Look Once) YOLO network, a fully connected neural network, and/or a combination of such networks.

In an embodiment, the one or more AI models 108 may correspond to language models. In such a case, the training and maintenance of language models like large language models (LLMs) involves an iterative process designed to ensure they remain accurate, relevant, and aligned with contemporary knowledge. The initial training phase consists of pre-training on vast datasets that include text from books, websites, and other publicly available sources. This stage focuses on teaching the model linguistic patterns, grammar, and basic reasoning abilities. However, pre-training alone may be insufficient for maintaining long-term accuracy or incorporating new developments. Therefore, such language models are periodically fine-tuned. The fine-tuning of language models may correspond to a process in which the language models are updated using more targeted and specific datasets. This fine-tuning enables the language models to adjust to new information, such as advancements in science, evolving societal norms, or emergent trends, ensuring their knowledge base is reflective of the latest data. As an exemplary implementation, the language models may be updated periodically (say weekly, monthly, or yearly) as required.

The server 110 may include suitable logic, circuitry, and interfaces, and/or code that may be configured to store the patient data and the medical data. The server 110 may be further configured to store the one or more medical databases 106. The server 110 may be implemented as a cloud server and may execute operations through web applications, cloud applications, HTTP requests, database operations, file transfer, and the like. Other example implementations of the server 110 may include, but are not limited to, a database server, a file server, a web server, a media server, an application server, a mainframe server, or a cloud computing server.

In at least one embodiment, the server 110 may be implemented as a plurality of distributed cloud-based resources by use of several technologies that are well known to those ordinarily skilled in the art. A person with ordinary skill in the art will understand that the scope of the disclosure may not be limited to the implementation of the server 110 and the IV pole 102 as two separate entities. In certain embodiments, the functionalities of the server 110 can be incorporated in its entirety or at least partially in the IV pole 102, without a departure from the scope of the disclosure.

The communication network 112 may include a communication medium through which the IV pole 102, the one or more data sources 104, the one or more medical databases 106, the one or more AI models 108, and the server 110 may communicate with each other without interruption during relocation. The communication network 112 may be one of a wired connection or a wireless connection. Examples of the communication network 112 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the network environment 100 may be configured to connect to the communication network 112 in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols. The IV pole 102 is equipped with advanced wireless communication modules, including Wi-Fi, Bluetooth, and cellular connectivity, to ensure consistent data transmission even when moving between different network zones within a facility.

In operation, the IV pole 102 may be configured to obtain the patient data associated with the patient 114 from the one or more data sources 104. The one or more data sources 104 may include at least one of a set of diagnostic medical devices associated with the patient 114, a set of monitoring devices associated with the patient 114, a set of scanning devices associated with the patient 114, a set of wearable devices associated with the patient 114, a set of fluid administration devices associated with the patient 114, and a set of sensors that may be associated with the patient 114. Details about the one or more data sources 104 are provided, for example, in FIG. 3. During patient relocation, these devices remain connected to the IV pole 102, ensuring continuous data collection and monitoring.

The IV pole 102 is further designed to integrate with hospital systems to automatically update the patient's location during transfers. Using location tracking technologies such as RFID, GPS, or indoor positioning systems, the IV pole 102 communicates the patient's movement to healthcare providers, ensuring that all members of the care team are aware of the patient's current location and status.

The power management system of the IV pole 102 includes a rechargeable battery with sufficient capacity to power all integrated devices during relocation. This ensures that no interruption occurs in device operation, data collection, or communication when the IV pole 102 is disconnected from mains power during patient movement.

The IV pole 102 may be further configured to retrieve one or more electronic medical health records (EHRs) associated with the patient based on the obtained patient data. The EHRs may include past medical history associated with the patient 114. The IV pole 102 may be further configured to retrieve, from the one or more medical databases 106, medical data associated with the patient based on a correlation of the patient data with the one or more electronic medical health records. Details about the correlation of the patient data with the one or more electronic medical health records are provided, for example, in FIG. 3.

Based on the retrieval of the medical data, the IV pole 102 may be further configured to apply the one or more AI models 108 to at least one of the patient data, the electronic medical health records, or the medical data. The IV pole 102 may be further configured to generate one or more alerts associated with a medical condition of the patient based on the application of the one or more AI models 108 to at least one of the patient data, the electronic medical health records, or the medical data. The IV pole 102 may be further configured to render the generated one or more alerts. Details about the one or more alerts are provided, for example, in FIG. 3.

Figure 2:
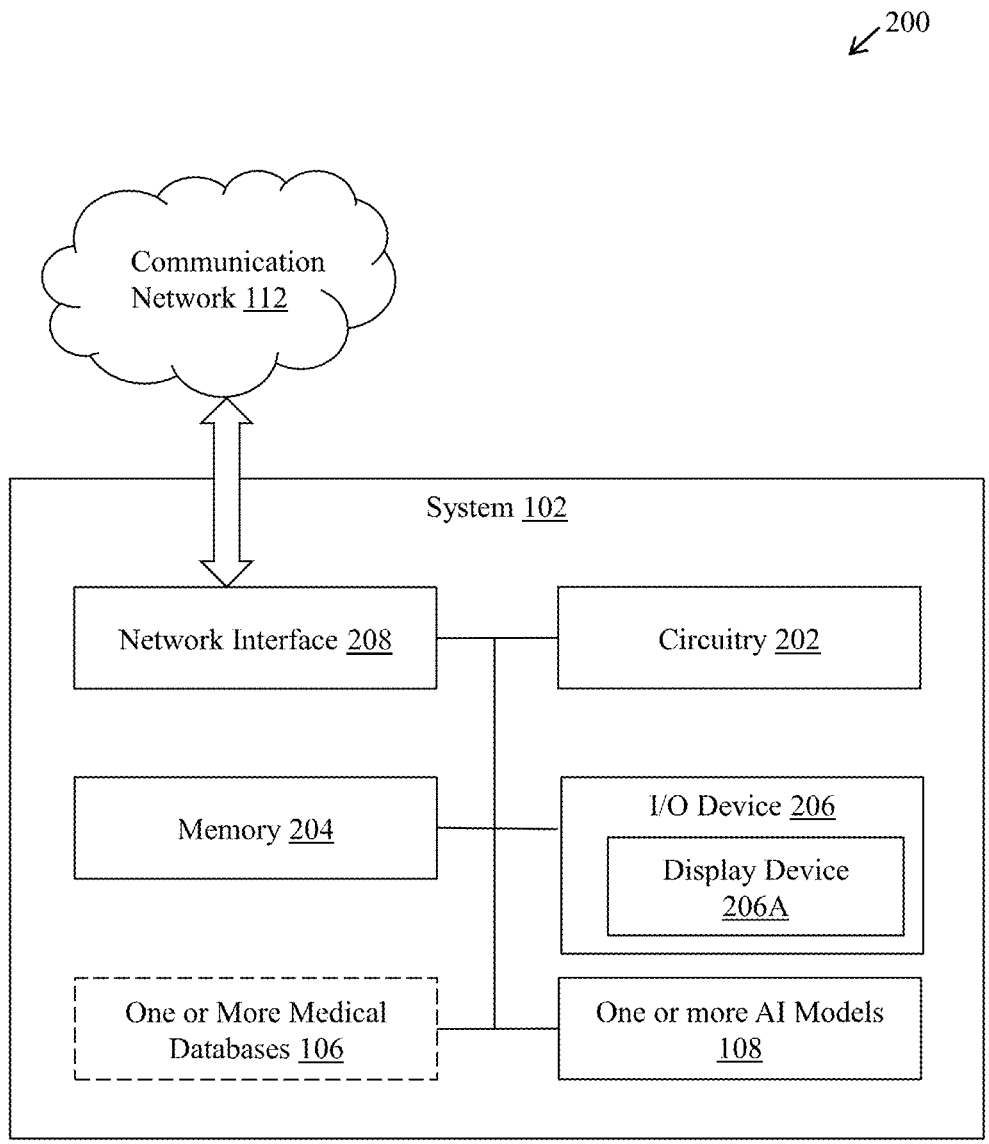
FIG. 2 is a block diagram that illustrates an exemplary intravenous pole for the generation of alerts, in accordance with an embodiment of the disclosure.

FIG. 2 is a block diagram that illustrates an exemplary intravenous pole optimized for mobility and continuous connectivity, for the generation of alerts, in accordance with an embodiment of the disclosure. FIG. 2 is explained in conjunction with elements from FIG. 1. With reference to FIG. 2, there is shown a block diagram 200 of the IV pole 102. The IV pole 102 may include a circuitry 202, a memory 204, an input/output (I/O) device 206, a network interface 208, one or more AI models 210, and the one or more medical databases 106. The circuitry 202 may be communicatively coupled to the memory 204, the I/O device 206, the network interface 208, the one or more AI models 108, and the one or more medical databases 106.

The circuitry 202 may include suitable logic, circuitry, and interfaces that may be configured to execute program instructions associated with different operations to be executed by the IV pole 102. For example, some of the operations may include, but are not limited to, obtaining the patient data, retrieving the one or more electronic medical health records, retrieving medical data, applying the one or more AI models 108, generating the one or more alerts associated with a medical condition of the patient 114, and rendering the generated one or more alerts. The circuitry 202 may include one or more specialized processing units, which may be implemented as an integrated processor or a cluster of processors that perform the functions of the one or more specialized processing units, collectively. The circuitry 202 may be implemented based on a number of processor technologies known in the art. Examples of implementations of the circuitry 202 may be an x86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other computing circuits.

The memory 204 may include suitable logic, circuitry, interfaces, and/or code that may be configured to store the program instructions to be executed by the circuitry 202. In at least one embodiment, the memory 204 may store the patient data, one or more EHRs, and medical data. In an embodiment, the memory 204 may be further configured to store one or more encryption techniques, location data, and the like. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may include suitable logic, circuitry, and interfaces that may be configured to receive one or more user inputs and provide an output. For example, the IV pole 102 may receive the user input via the I/O device 206. The I/O device 206 may further display the generated one or more alerts. The I/O device 206 which includes various input and output devices, may be configured to communicate with the circuitry 202. Examples of the I/O device 206 may include, but are not limited to, a set of visual indicators, an image capture sensor, a touch screen, a keyboard, a mouse, a joystick, a microphone, a display device 206A, and a speaker.

The display device 206A may include suitable logic, circuitry, and interfaces that may be configured to display the generated one or more alerts. The display device 206A may be further configured to display the patient data, the one or more EHRs, or the medical data. The display device 206A may be a touch screen which may enable a user to provide a user-input via the display device 206A. The touch screen may be at least one of a resistive touch screen, a capacitive touch screen, or a thermal touch screen. The display device 206A may be realized through several known technologies such as, but not limited to, at least one of a Liquid Crystal Display (LCD) display, a Light Emitting Diode (LED) display, a plasma display, or an Organic LED (OLED) display technology, or other display devices. In accordance with an embodiment, the display device 206A may refer to a display screen of a head mounted device (HMD), a smart-glass device, a see-through display, a projection-based display, an electro-chromic display, or a transparent display.

The network interface 208 may include suitable logic, circuitry, and interfaces that may be configured to facilitate a communication between the circuitry 202, the one or more data sources 104, the one or more medical databases 106, and the server 110, via the communication network 112. The network interface 208 may be implemented by use of various known technologies to support wired or wireless communication of the IV pole 102 with the communication network 112. The network interface 208 may include, for example, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry.

The network interface 208 may be configured to communicate via wireless communication with networks, such as the Internet, an Intranet, or a wireless network, such as a cellular telephone network, a public switched telephonic network (PSTN), a radio access network (RAN), a wireless local area network (LAN), and a metropolitan area network (MAN). The wireless communication may use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VOIP), light fidelity (Li-Fi), Worldwide Interoperability for Microwave Access (Wi-MAX), a protocol for email, instant messaging, and a Short Message Service (SMS).

In an embodiment, at least one AI model of the one or more AI models 108 may correspond to a sophisticated artificial intelligence (AI) system trained on vast amounts of text data, capable of understanding, generating, and processing human-like language at an extensive scale. The at least one AI model utilizes deep learning techniques, particularly transformer architectures, enabling them to grasp context, syntax, semantics, and even nuances in language usage. The primary function of the at least one AI model may involve, but is not limited to, natural language processing tasks like text generation, translation, summarization, and sentiment analysis. The at least one AI model may learn to predict and generate text by analyzing patterns and relationships within the massive corpus of text they've been trained on. Examples of different types of the at least one AI model may include, but are not limited to, a Transformer-Based Model, a Bidirectional Encoder Representations from Transformers (BERT) model, a Generative Pre-trained Transformer (GPT) model, a Unified Language Model, and a Text-to-Text Transfer Transformer (T5) model.

The network interface 208 is specifically designed to maintain communication across different network infrastructures within a healthcare facility. It supports seamless handoff between Wi-Fi access points and can switch to cellular networks if Wi-Fi is unavailable, ensuring that data connectivity is uninterrupted during movement.

The functions or operations executed by the IV pole 102, as described in FIG. 2, may be performed by the circuitry 202. Various operations executed by the circuitry 202 are described in detail, for example, in FIGS. 3, 4, and 5.

Figure 3:
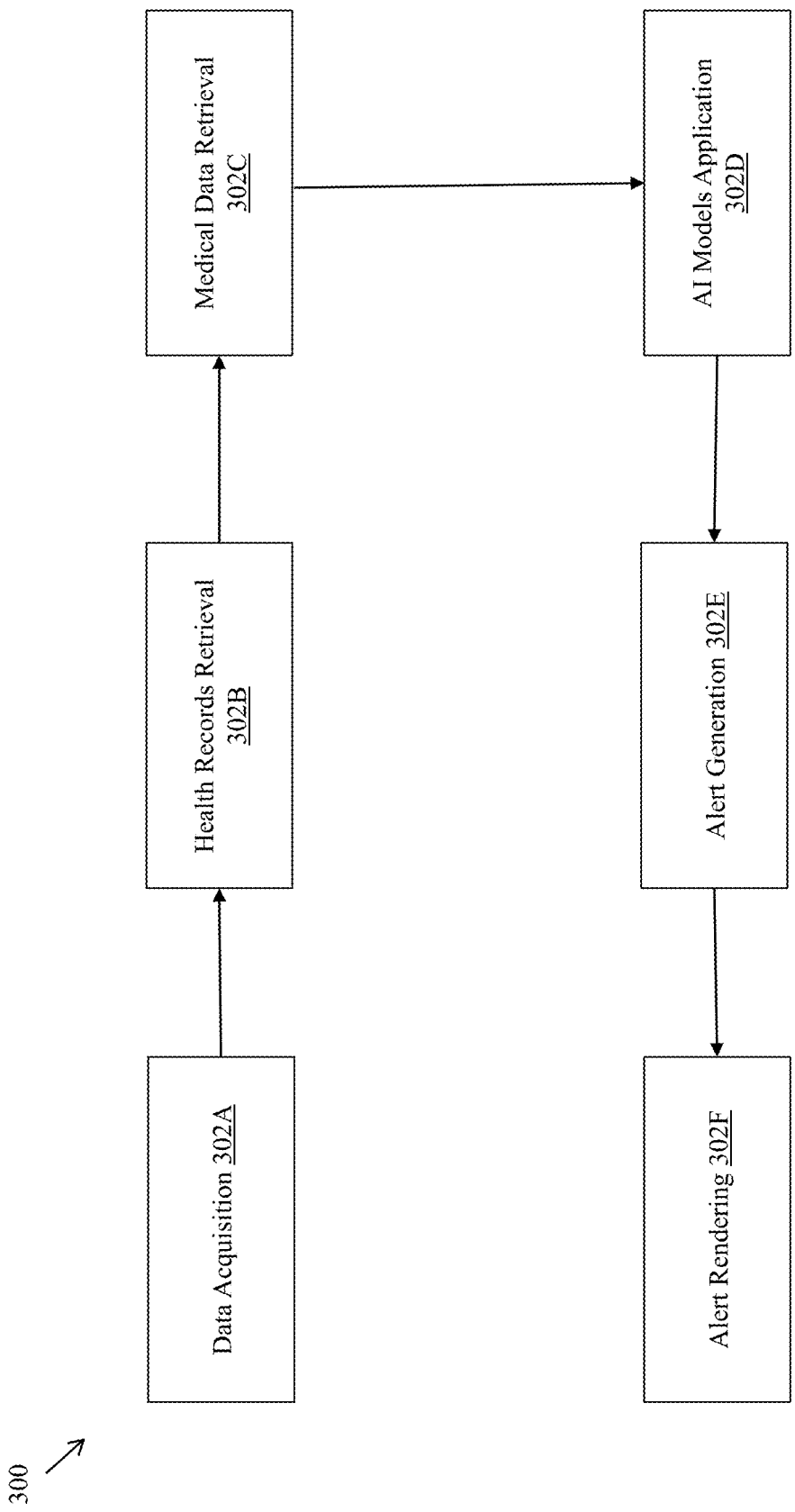
FIG. 3 is a diagram that illustrates exemplary operations for for generation of alerts by an intravenous pole, in accordance with an embodiment of the disclosure.

FIG. 3 is a diagram that illustrates exemplary operations for generation of alerts by an intravenous pole, even during or after patient relocation in accordance with an embodiment of the disclosure. FIG. 3 is explained in conjunction with elements from FIG. 1 and FIG. 2. With reference to FIG. 3, there is shown a block diagram 300 that illustrates exemplary operations from 302A to 302F, as described herein. The exemplary operations illustrated in the block diagram 300 may start at 302A and may be performed by any computing system, apparatus, or device, such as by the IV pole 102 of FIG. 1 or the circuitry 202 of FIG. 2. Although illustrated with discrete blocks, the exemplary operations associated with one or more blocks of the block diagram 300 may be divided into additional blocks, combined into fewer blocks, or eliminated, depending on the particular implementation.

At 302A, a data acquisition operation may be performed. In data acquisition operation, the circuitry 202 may be configured to obtain the patient data. The patient data may be obtained from the one or more data sources 104 and may be associated with the patient 114. The patient data may be indicative of vitals associated with the patient and may include, but is not limited to, a heart rate, a blood oxygen rate, a blood pressure, a respiratory rate, an X-ray report, and an ultrasound report.

In an embodiment, the patient 114 may be suffering from a medical condition (say a disease) and may be admitted to a medical facility (say a hospital). The set of diagnostic medical devices may be configured to capture the first medical data associated with the patient 114. In an embodiment, the set of diagnostic medical devices may further include a set of diagnostic medical devices and a set of monitoring devices.

Each of the set of diagnostic medical devices may correspond to instruments or tools that may be used by healthcare professionals to identify and diagnose the medical conditions in the patient 114. Each of the set of diagnostic medical devices may often provide quantitative or qualitative data about the health status of the patient 114. Such data may be useful in determining an appropriate course of treatment for the medical condition. In an embodiment, the set of diagnostic medical devices may include, but are not limited to, a blood glucose monitor, an electrocardiogram (ECG or EKG) machine, a spirometer, and a sphygmomanometer.

Each of the set of monitoring devices may correspond to instruments that may be designed to observe and track various physiological parameters or medical conditions in the patient 114. Each of the set of monitoring devices may provide real-time data, enabling healthcare professionals to make informed decisions about patient care and treatment adjustments. Examples of such monitoring devices may include, but are not limited to, a pulse oximeter, a glucose monitor, a heart monitor, a blood pressure monitor, a cardiac monitor, a respiratory rate monitor, a sleep apnea monitor, an intracranial pressure monitor, and a wearable fitness tracker.

In an embodiment, the first medical data may be received from the set of scanning devices. Each of the set of scanning devices may correspond to equipment that may be used in healthcare settings to obtain detailed images or scans of internal structures within the human body for diagnostic or monitoring purposes. Examples of the set of scanning devices may include, but are not limited to, an X-ray machine, an MRI (Magnetic Resonance Imaging) scanner, a CT (Computed Tomography) scanner, an ultrasound machine, a Positron Emission Tomography (PET) Scanner, a Single-Photon Emission Computed Tomography (SPECT) Scanner, a Mammography Machine, and an ultrasound machine.

In an embodiment, the IV pole 102 may be configured to receive the first medical data associated with the patient 114 from the set of diagnostic medical devices or the set of scanning devices. As discussed above, both the set of diagnostic medical devices and the set of scanning devices may be included in the one or more data sources 104. In an embodiment, the first medical data may correspond to at least one of a medical professional's prescription note, a pathology report, an X-radiation (X-RAY) report, a computed tomography (CT) report, a magnetic resonance imaging (MRI) report, an ultrasound report, a cardiac catheter report, or a cardiac stress report associated with the patient 114.

In an alternate embodiment, the one or more data sources 104 may include a set of wearable devices associated with the patient. The set of wearable devices associated with the patient may be worn by the patient 114 and may include, but are not limited to, a Fitness Tracker, a Smartwatches with Health Features, a Continuous Glucose Monitors, an ECG Monitor, a Blood Pressure Monitor, a Wearable ECG Patch, a Pulse Oximeter, or a Medication Adherence Tracker. Details about the set of wearable devices are known in the art and therefore, have been omitted for the sake of brevity.

In an embodiment, the one or more data sources 104 may further include the set of fluid administration devices associated with the patient 114. Each of the set of fluid administration devices associated with the patient 114 may correspond to devices that may be configured to deliver fluids, medications, and nutrients to the patient 114. The set of fluid administration devices associated with the patient 114 may include, but are not limited to, an Intravenous (IV) Cannulas and Catheters, IV Drip Sets, Infusion Pumps, Enteral Feeding Pumps and Syringes, Hypodermoclysis Devices, and the like. Details about the set of fluid administration devices are known in the art and therefore, have been omitted for the sake of brevity.

In yet another embodiment, the one or more data sources 104 may further include the set of sensors. The set of sensors may include, but are not limited to, an image capture sensor, a heart rate monitoring sensor, and a blood oxygen monitoring sensor. In case the patient data is captured by the image capture sensor, then the patient data may correspond to an image of the patient, or a wound of the patient, or the like.

At 302B, a health records retrieval operation may be executed. In the health records retrieval operation, the IV pole 102 may be configured to retrieve the one or more electronic medical health records (EHRs) associated with the patient 114. In an embodiment, the one or more EHRs may be retrieved based on the obtained patient data. The one or more EHRs may correspond to historical health records related to the patient and may be indicative of one or more diseases related to the patient 114, a time period indicative of a time since when the patient 114 may be suffering from the one or more diseases, one or more medicines that may be taken by the patient 114, and the like.

Further, at 302B, a mobility-aware health records retrieval operation may be executed. The IV pole 102 retrieves the electronic medical health records associated with the patient based on the obtained patient data, even as the patient is being relocated. The system ensures that data access and retrieval times are optimized to prevent delays during critical transfers.

At 302C, a medical data retrieval operation may be executed. In the medical data retrieval operation, the IV pole 102 may be configured to retrieve, from the one or more medical databases 106, medical data associated with the patient 114. To retrieve the medical data, the IV pole 102 may be configured to co-relate the patient data with the one or more EHRs. The correlation of the patient data with the one or more EHRs may correspond to an association of the patient data with the one or more EHRs. The medical data may be retrieved based on a correlation of the patient data with the one or more electronic medical health records. The medical data may be retrieved from the MDG's (knowledge database related to the medical field) and may be indicative of curing the one or more diseases from which the patient 114 may be suffering. Alternatively, the medical data may be indicative of medicines that may have to be provided to the patient 114 based on the current patient data and the one or more EHRs.

Further, at 302C, a continuous medical data retrieval operation is performed. The IV pole 102 retrieves medical data from the one or more medical databases 106 based on the correlation of patient data and electronic medical health records, maintaining this functionality during relocation without interruption.

At 302D, an AI models application operation may be executed. In the AI models application operation, the IV pole 102 may be configured to apply the one or more AI models 108 to at least one of the patient data, the electronic medical health records, or the medical data. As discussed above, the one or more AI models 108 may be pre-trained to analyze the patient data, the one or more EHRs, and the medical data and generate one or more alerts. Details about the one or more AI models 108 are provided, for example, in FIG. 1.

Further, at 302D, the application of AI models takes into account rapid patient relocation. The one or more AI models 108 are applied to assess any potential risks associated with relocation, such as changes in vital signs due to movement, and generate alerts accordingly.

At 302E, an alert generation operation may be executed. In the alert generation operation, the IV pole 102 may be configured to generate one or more alerts associated with a medical condition of the patient 114. The medical condition of the patient 114 may be indicative of the one or more current medical problems that may be faced by the patient 114. In an embodiment, the one or more alerts associated with a medical condition of the patient 114 may be generated based on the application of the one or more AI models 108 to at least one of the patient data, the electronic medical health records, or the medical data.

Further, at 302E, alerts generated are communicated to healthcare providers in real-time, with consideration for the patient's changing location. The IV pole 102 ensures that alerts are routed to the appropriate personnel based on the current location within the facility.

At 302F, an alert rendering operation may be executed. In the alert rendering operation, the IV pole 102 may be configured to render the generated one or more alerts. In an embodiment, the generated one or more alerts may be rendered on a display device 206A associated with the IV pole. Details about the display device 206A are provided, for example, in FIG. 2.

Further, at 302F, the IV pole 102 renders the generated alerts via its integrated display and communicates them to connected devices or systems, ensuring that the information is accessible to healthcare providers regardless of the patient's movement status.

In an alternate embodiment, the IV pole 102 may be further configured to encrypt the patient data, the one or more electronic medical health records, or the one or more alerts. In an embodiment, the one or more electronic medical health records, or the one or more alerts may be encrypted using one or more encryption techniques. Once encrypted, the IV pole 102 may be configured to transmit, via the network interface, the encrypted patient data, the encrypted one or more electronic medical health records, or the encrypted one or more alerts to at least one electronic device of a set of electronic devices. The set of electronic devices may be associated with the set of medical professionals (such as doctors, nurses, and the like) who may be treating the patient 114 for their analysis. The patient data, the one or more electronic medical health records, or the one or more alerts may be encrypted using the one or more encryption techniques so that the patient data, the one or more electronic medical health records, or the one or more alerts is not modified by malicious users during the transmission. In an embodiment, the one or more encryption techniques may include at least one of an Advanced Encryption Standard (AES) technique, a Data Encryption Standard (DES) technique, a Triple Data Encryption Standard (3DES) technique, a Rivest-Shamir-Adleman (RSA) technique, an Elliptic Curve Cryptography (ECC) technique, and a Blowfish (BF) technique. In an embodiment, the IV pole 102 may be configured to encrypt all the data before transmission to other devices.

Figure 4:
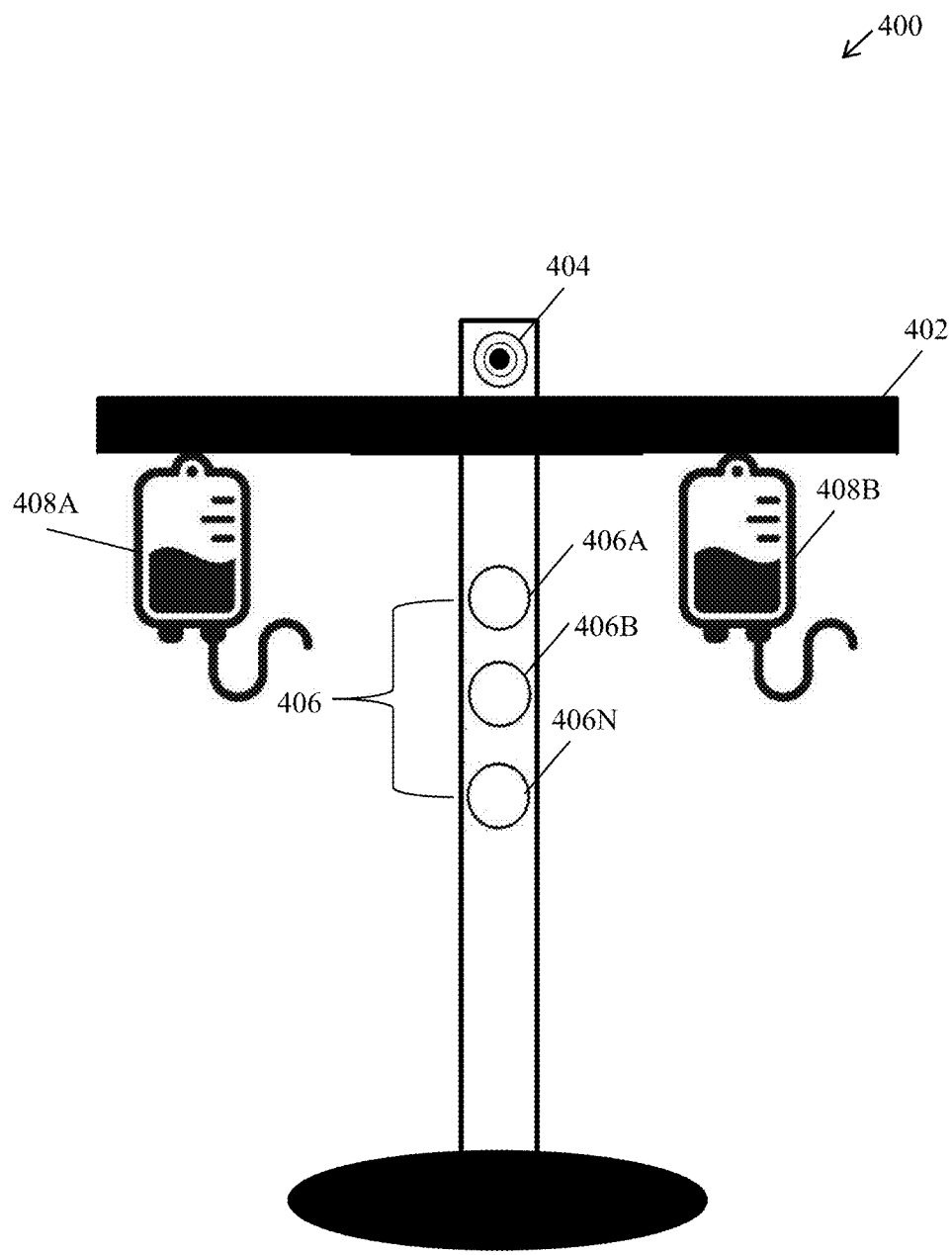
FIG. 4 is a diagram that illustrates an exemplary IV pole, in accordance with an embodiment of the disclosure.

FIG. 4 is a diagram that illustrates an exemplary IV pole designed for mobility and uninterrupted connectivity, in accordance with an embodiment of the disclosure. FIG. 4 is explained in conjunction with elements from FIG. 1, FIG. 2, and FIG. 3. With reference to FIG. 4, there is shown a diagram 400 that includes an IV pole 402. The IV pole 402 may be an exemplary embodiment of the IV pole 102 of FIG. 1.

In an embodiment, the IV pole 402 may be a smart device that may include an image capture sensor 404. The image capture sensor 404 includes suitable logic, circuitry, and interfaces that may be configured to capture one or more images of the patient and the 3D physical space around the patient. During relocation, the image capture sensor 404 continues to monitor the patient, providing real-time visual data to healthcare providers. Examples of each of the image capture sensors 404 may include, but are not limited to, a depth sensor, a wide-angle camera, an action camera, a closed-circuit television (CCTV) camera, a camcorder, a digital camera, camera phones, a time-of-flight camera (ToF camera), a night-vision camera, and/or other image capture devices.

In an embodiment, the image capture sensor 404 may be positioned at the top of the IV pole 402. This may allow the IV pole to continuously monitor the patient's condition, detect potential risks like falls, improper wound care, or pressure sores, and alert medical staff in real-time. Therefore, the IV pole 402 is equipped with a camera system at the top, utilizing AI-driven software to monitor the patient's condition. Such a configuration may detect changes in patient behaviour or status and alert medical staff in real-time, thereby enhancing patient care through continuous monitoring and analysis.

The IV pole 402 includes enhanced mobility features such as omni-directional casters with locking mechanisms, a stable and weighted base to prevent tipping during movement, and handles ergonomically placed for easy manocuvring by healthcare staff.

In an embodiment, the IV pole 402 may be configured to control the image capture sensor 404 to capture an image of a wound of the patient 114. The patient data includes the captured image. The IV pole 402 may be further configured to apply a first AI model of the one or more AI models 108 on the captured image. The IV pole 402 may be configured to generate the one or more alerts associated with the medical condition of the patient based on the application of the first AI model on the captured image.

In an embodiment, the image capture sensor 404 integrated into the IV pole 402 leverages photoplethysmography (PPG), video-based photoplethysmography (vPPG), and Pulse Transit Time (PTT) technologies to continuously monitor a patient's heart rate and blood pressure. In such an implementation, the IV pole 402 employs two spatially separated image capture sensors that provide a depth view of the patient 114 and their environment, enabling highly accurate determination of patient position, location, and movement down to millimeter precision. Such configuration also allows the IV pole 402 to monitor the elevation of the bed's head over time-critical for intubated patients- and to non-invasively measure chest excursion, essential for monitoring respiratory rate and detecting conditions like respiratory depression or narcotic overdose. During relocation, the image capture sensor 404 continues to monitor the patient, providing real-time visual data to healthcare providers.

It may be noted that by embedding advanced monitoring technologies into the IV pole 402, the IV pole 402 is transformed from a mere support structure into a vital, active element of patient monitoring. The image capture sensor 404, mounted at the top of the pole, captures subtle changes in the patient's skin associated with vital signs. The IV pole 402 then analyzes these changes in real-time using the one or more AI models 108 to deliver accurate, non-invasive measurements of heart rate and blood pressure, crucial for patient care.

In addition to vital sign monitoring, the image capture sensor 404 also enhance patient-positive identification by visually verifying that the patient in the bed matches the photo stored in the hospital's ADT system and electronic medical records (EMR). Through facial recognition, the IV pole 402 ensures that the identity of the patient 114 is accurately confirmed, and that the vital sign data being collected is correctly associated with the right patient's electronic medical record. This added layer of verification helps prevent medical errors and enhances overall patient safety.

Therefore, this application not only allows for continuous, real-time data collection without the need for additional, intrusive equipment but also ensures that these capabilities are seamlessly integrated into an essential piece of medical equipment. Enhanced by AI-driven analytics, the system refines the accuracy of its measurements, providing healthcare providers with reliable, actionable data. The innovative use of PPG, vPPG, PTT, and facial recognition within the context of the IV pole 402 represents a significant advancement in patient monitoring, with lifesaving implications for busy emergency rooms, understaffed nursing floors, and mass casualty events.

In an embodiment, the image capture sensor 404 integrates seamlessly into the IV pole 402, encompassing hardware components, software algorithms, and connectivity with the IT infrastructure of the medical facility such as the hospital. Such integration may be useful in fall risk monitoring, wound care verification, pressure sore prevention, and integration with hospital systems.

In an embodiment, the IV pole 402 may be configured to obtain, from the one or more data sources 104, the patient data associated with the patient 114. The one or more data sources 104 include at least one of the sets of wearable devices associated with the patient, and the set of sensors. The IV pole 402 may be further configured to apply a second AI model of the one or more AI models 108 on the obtained patient data. The patient data may include at least one of accelerometer data associated with a movement of the patient 114, or gyroscopic data associated with the movement of the patient 114. The IV pole 402 may be further configured to generate the one or more alerts associated with the medical condition of the patient based on the application of the second AI model on the obtained patient data.

In another embodiment, the IV pole 402 may be configured to apply a third AI model of the one or more AI models 108 on the obtained patient data and generate the one or more alerts associated with the medical condition of the patient 114 based on the application of the third AI model on the obtained patient data. The one or more alerts are indicative of a repositioning of the patient to prevent one or more pressure sores associated with the patient 114.

In an alternate embodiment, by utilizing the one or more AI models 108, the IV pole 402 monitors patient movements to detect potential fall risks and alert medical staff promptly, allowing for timely intervention. The IV pole 402 ensures compliance with prescribed wound care routines by monitoring activities such as dressing changes and patient repositioning. The IV pole 402 documents these activities in the patient's electronic health record (EHR) to maintain accurate records. Furthermore, The IV pole 102 monitors patient positions and detects when a patient has been immobile for extended periods, alerting medical staff to reposition the patient, thereby reducing the risk of pressure sores. Moreover, the IV pole 402 with the image capture sensors 404 is designed for seamless integration with existing hospital IT systems, including Electronic Health Records (EHRs). The IV pole 402 supports real-time documentation and alerting, ensuring that all relevant data is communicated to mobile devices and nurse stations for timely interventions.

In an embodiment, the IV pole 402 includes a set of visual indicators 406. The set of visual indicators may include a first visual indicator 406A, a second visual indicator 406B, up to an Nth visual indicator 406N. The IV pole 402 may be configured to control a display of a first color in a first visual indicator 406A of the set of visual indicators 406 based on the patient data.

In an embodiment, the top of the IV pole 402 features a set of visual indicators that change colors (green, yellow, red) based on alerts from connected medical devices. Such configuration provides immediate visual feedback on the patient's status. In scenarios where a patient is in distress (e.g., waiting areas or mass casualty events), the visual alerts may prompt others to call for immediate assistance, thereby helping to identify and respond to critical situations swiftly.

In an embodiment, the disclosed IV pole 402 is equipped with patient identification and verification technology, wherein if an unauthorized or incorrect patient enters the bed or if no patient has been associated with the bed, the IV pole 402 triggers an audible chirp or alarm and a visual alert using the integrated LED light system to notify medical staff of the discrepancy, ensuring patient safety and preventing potential errors in care.

In an embodiment, the disclosed IV pole 402 is designed for use in mass casualty situations where it can be deployed on stretchers, gurneys, and other triage platforms. The specialized app and visual alert system enhance triage efficiency, enabling rapid patient identification and communication with medical personnel. The disclosed IV pole 402 ensures that even in chaotic environments, patients can be quickly and accurately triaged, improving overall response times and outcomes. In an alternate embodiment, the IV pole 402 is equipped with an enhanced positive patient identification system, including a network jack connection at each bed that is uniquely identified by its location within the hospital's ADT (Admission, Discharge, and Transfer) system. A magnetic cable with a dongle connects the IV pole to the network jack, automatically assigning the pole to the specific bed location. Upon connection, the IV pole is linked to the patient assigned to that bed through the ADT system, with additional verification provided by scanning the patient's bracelet using an integrated barcode reader or RFID chip scanner embedded in the IV pole.

In an embodiment, the IV pole 402 is connected with one or more display devices using a customized active cable arrangement. Specifically, the IV pole 402 includes the active cable arrangement that connects medical devices to external displays for enhanced data visualization and patient monitoring. This ensures that critical data is readily available to healthcare providers, whether the pole is attached to a stretcher, gurney, wheelchair, or other platform. Details about the active cable arrangement are provided in a patent application with application number U.S. Pat. No. 11,309, 665, titled "Active cable arrangement for connecting medical devices to a display".

In an embodiment, the IV pole 402 is integrated into a Real-Time Location System (RTLS), utilizing embedded sensors and transceivers to precisely locate and track in real-time medical staff, equipment, and other assets within the healthcare facility, enhancing operational efficiency, patient safety, and resource management.

In an embodiment, the IV pole 402 may be configured to receive a set of instructions associated with an administration of one or more fluids from one or more fluid bags 408A and 408B to the patient 114. The IV pole 402 may be configured to control a flow rate of the one or more fluids to the patient based on the received set of instructions. Specifically, the IV pole 402 is equipped with integrated sensors and monitoring systems capable of measuring and tracking the administration of intravenous (IV) fluids in real-time, thereby providing accurate data on fluid flow rates, and volume administered, and alerting medical staff to any irregularities or deviations from prescribed treatment plans.

In an embodiment, the IV pole 402 may implement a variety of communication protocols for Wireless Fidelity (Wi-Fi) connectivity, long-range (LoRa) connectivity, cellular connectivity, and the like. The Wi-Fi connectivity may enhance data transmission between the IV pole 402 and hospital IT systems, supporting real-time updates to Electronic Health Records (EHRs) and other platforms. The LoRa connectivity enables long-range, low-power communication, making the IV pole a reliable conduit for connecting wearable medical devices across a hospital or medical facility or even outside during a mass casualty event. The cellular connectivity provides robust, high-speed connectivity, ensuring uninterrupted communication even in areas with limited Wi-Fi coverage. The integration of a cellular network (such as 5G) within the mesh network allows for scalable and reliable data transfer between multiple IV poles.

In another embodiment, the IV pole 402 may be capable of forming a mesh network, allowing communication and data transfer between multiple poles in a ward or triage area. This mesh network may be configured so that one bed within a ward has 5G connectivity, enabling all other beds to connect either through the hospital's Wi-Fi system or via cellular connection through the mesh network. This feature ensures continuous and reliable data communication even in scenarios where Wi-Fi coverage may be limited or interrupted.

The IV pole 402 integrates the Integrated Medical Device Data System (MDDS) Components, LoRa connectivity, and the Medical Data Governance System (MDGS) to ensure secure and centralized data management. LoRa technology enhances long-range, low-power communication capabilities, enabling the system to connect with wearable medical devices across extended distances within a hospital or outside a hospital during events like mass casualties. Furthermore, blockchain technology is employed to verify and protect patient data integrity, facilitating precise diagnosis and treatment across different medical environments.

Specifically, Blockchain technology in the IV Pole 402 focuses on ensuring the integrity of data at the point of collection. Blockchain in the IV Pole 402 is used to verify the integrity of data collected from connected devices (e.g., infusion pumps, patient monitors). The blockchain ensures that the data is cryptographically signed and verified before it leaves the IV Pole, ensuring that the data hasn't been tampered with. Before transmitting the data to the MDG system, the IV Pole uses blockchain to verify that the information coming from attached medical devices is accurate and secure. This acts as an integrity check at the local device level. Once the IV Pole verifies the integrity of the data using blockchain, it transmits the data to the MDG. In this series-based flow, the blockchain in the IV Pole focuses on initial verification, while the MDG's blockchain ensures secure governance of data as it moves across the hospital's systems.

Furthermore, there are several other benefits of implementing blockchain technology such as enhanced data security as blockchain's encryption and decentralized storage provide superior protection for sensitive health data. Even if one node is compromised, the data remains safe and unchanged across the network. Other benefits include but are not limited to, Improved Data Accuracy, Auditability and Traceability, Regulatory Compliance, Scalability, Flexibility, and Cost Efficiency. Generally, Blockchain ensures that patient information, such as IV administration records and vital signs, remains consistent and free from unauthorized modifications thereby providing data accuracy. Blockchain creates a transparent and auditable history of all data transactions, enabling compliance with regulatory requirements such as Food and Drug Administration (FDA 21 CFR Part 820) and International Organization for Standardization (ISO) 13485, thereby ensuring auditability and traceability. Blockchain supports compliance with regulations by ensuring data integrity and traceability, aligning with standards like FDA Medical Device Data Systems (MDDS) and International Electrotechnical Commission (IEC) 62304 for software lifecycle processes, thereby complying with regulatory compliance. Blockchain minimizes operational costs by reducing the need for intermediaries and simplifying secure data transmission across medical devices and systems thereby ensuring cost efficiency. The decentralized architecture allows the IV Pole 402 to scale seamlessly within hospital networks or extend to other healthcare facilities, without sacrificing data integrity thereby providing Scalability and Flexibility.

In conclusion, the integration of blockchain technology in both the IV Pole 402 and the MDG framework ensures that patient data is securely managed from the point of collection to its governance within the hospital infrastructure. Blockchain provides enhanced security, data integrity, and regulatory compliance, making it a vital component of modern medical data management.

Also, the IV pole 402 features Bluetooth Localization. Specifically, a near-range Bluetooth receiver and transmitter are mounted near the top of the IV pole 402, allowing for the precise localization of Bluetooth devices within a one- to two-meter radius. This feature ensures that Bluetooth-enabled devices can be accurately associated with the correct bed or stretcher, improving the reliability of patient monitoring and device management.

Furthermore, the IV pole 402 features Location Tracking Using Radio Frequencies. The IV pole 402 is equipped with technology that uses radio frequencies to triangulate its location in X, Y, and Z coordinates. This capability enables accurate tracking of the bed or stretcher's location within the hospital, ensuring precise monitoring and record-keeping.

In an embodiment, the IV pole 402 implements AI-Driven Data Governance and Analytics. The IV pole 402 includes AI-driven data governance capabilities as discussed in the US patent application with application number U.S. Pat. No. 12,001,464, titled "System and method for medical data governance using large language models". The IV pole 402 manages and analyzes data from connected devices. This feature enhances data accessibility, and security, and provides predictive analytics to support clinical decision-making across different care environments.

Furthermore, the IV pole 402 implements wearable device integration. Specifically, the IV pole The IV pole is compatible with wearable devices as described in the US patent application with application number U.S. Pat. No. 12,002,579, titled "Wearable medical device data connectivity system and method". The IV pole 402 may receive data from wearable medical devices and integrate it into the hospital's electronic medical records (EMRs), allowing continuous patient monitoring and real-time data updates regardless of the patient's location within the hospital or triage area.

Furthermore, the IV pole 402 features a real-time communication system. The IV pole 402 features real-time communication capabilities, allowing direct interaction between patients and medical staff via a specialized smartphone app. This specialized smartphone app supports push-to-talk, texting, video communication, and more, enabling seamless communication with a nurse's station. This feature is particularly useful in waiting areas and triage zones, where quick communication can significantly improve patient outcomes. The IV pole 402 can also integrate into a hospital's existing nurse call system with a wireless adapter between a bedside nurse call controller and the wall jack or by a wireless nurse call controller integrated into the back-end server of the hospital's nurse call system.

Furthermore, the IV pole 402 includes a hot-swappable, rechargeable battery that powers its internal systems. The IV pole 402 is also equipped with an external accessory battery connection and electrical cord to ensure continuous operation, particularly in high-demand situations like mass casualty events. The battery management system (BMS) integrated into the IV pole 402 ensures safe and efficient operation by providing overcharge protection, thermal management, and continuous monitoring of battery health. The BMS also interfaces with the hospital's IT infrastructure, delivering real-time updates on the battery's status to ensure uninterrupted operation.

Furthermore, the IV pole 402 is designed to be universally adaptable, and capable of integration with stretchers, gurneys, wheelchairs, waiting area chairs, and triage stretchers. The base of the IV pole 402 is custom-designed to fit specific manufacturers' equipment, allowing the pole itself to be universally attached to any base. This design ensures that the IV pole 402 may be easily integrated into various medical platforms while maintaining its lightweight and functional properties. The IV pole 402 itself functions as an antenna for wireless communication, utilizing its height and separation from other medical devices to reduce electromagnetic interference (EMI). This design improves data transmission reliability, which is essential for maintaining the integrity of medical data in critical environments.

Furthermore, the IV pole 402 may include at least one antenna. In an embodiment, receive a first user input associated with retraction of the at least one antenna. The IV pole 402 controls the at least one antenna to retract inside the IV pole 402 based on the received first user input. Specifically, for use with stretchers, the IV pole is designed with a retractable mechanism such that both the IV pole and its integrated antenna can be retracted into a compact position to prevent damage during transport. When the IV pole is in its upright and extended position, the antenna is simultaneously extended to ensure optimal wireless communication and signal reception. A special variant for use to retrofit mass casualty stretchers.

It may be noted that the IV pole 402 provides decision support through predictive analytics, but the final medical decisions are still made by the medical professionals. The IV pole 402 alerts staff to critical changes, trends, or anomalies, allowing for faster intervention but does not autonomously make clinical decisions. Therefore, The IV pole 402 does not autonomously make decisions. It uses AI-driven analysis to assist medical professionals by generating alerts and recommendations based on real-time sensor data. All decisions are verified and acted upon by trained healthcare providers, ensuring that no critical interventions are made without human oversight.

The IV pole 402 is equipped with shock-absorbent mountings for all attached devices to protect sensitive equipment during movement over uneven surfaces or thresholds, ensuring device integrity and continuous operation. Furthermore, power supply continuity is ensured through a built-in battery backup system that powers all connected devices during relocation. The battery system is designed to provide sufficient power for extended transfers, such as moving patients between different departments or facilities.

The IV pole 402 integrates location tracking technologies. GPS or indoor positioning systems allow the IV pole to update the patient's location in real-time within the hospital's network, aiding in workflow coordination and resource allocation during patient transfers. Moreover, communication interfaces are designed to adapt to changing network environments during movement. The IV pole 402 automatically switches between available networks to maintain connectivity, utilizing technologies like Wi-Fi roaming and cellular data fallback options. Therefore, the design of the IV pole 402 allows for quick attachment and detachment of accessories and medical devices, facilitating rapid preparation for patient relocation. Standardized mounts and connectors ensure compatibility with a wide range of equipment.

Figure 5:
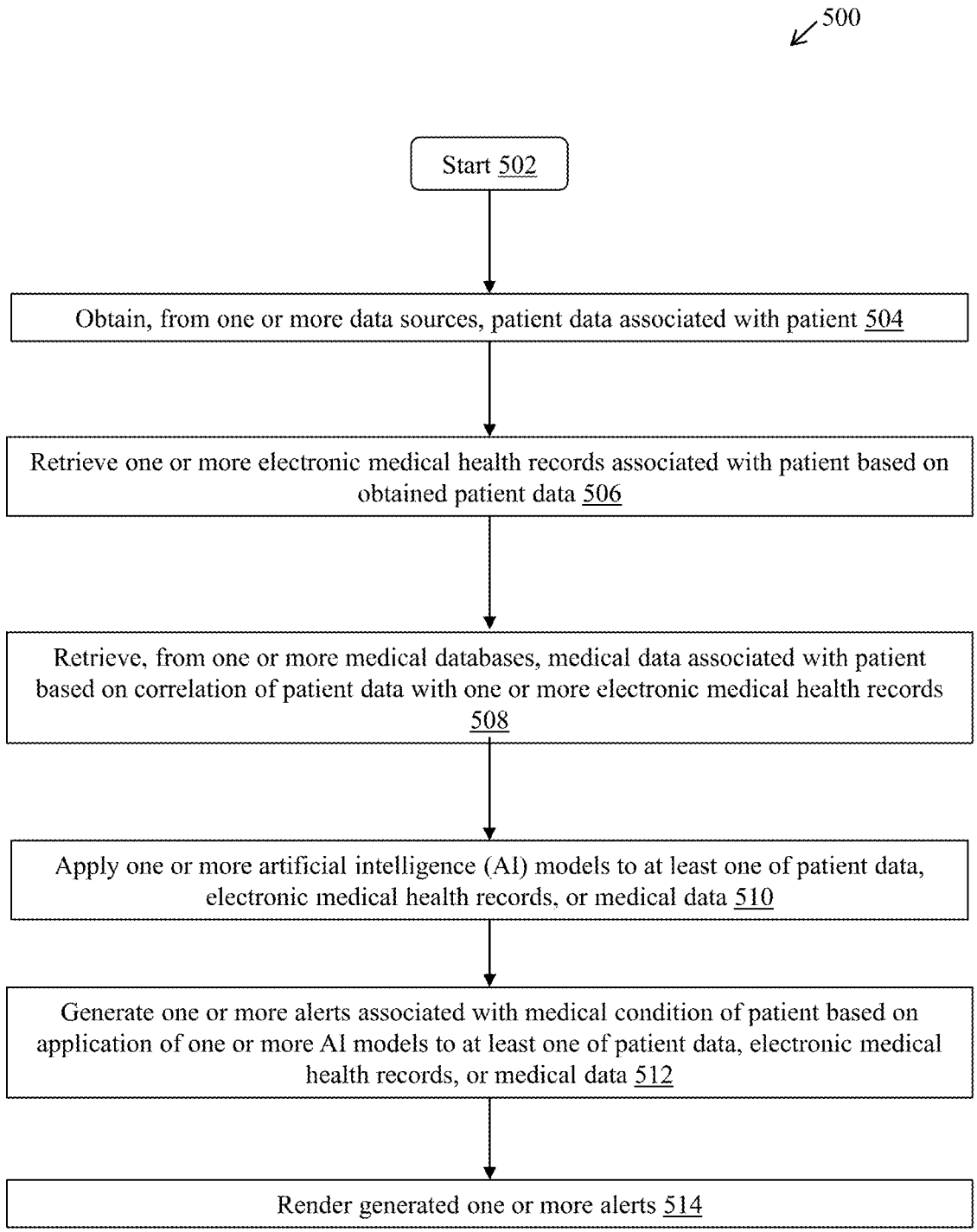
FIG. 5 is a flowchart that illustrates an exemplary method for the generation of one or more alerts by the IV pole, in accordance with an embodiment of the disclosure.

FIG. 5 is a flowchart that illustrates an exemplary method for the generation of one or more alerts by the IV pole, in accordance with an embodiment of the disclosure. FIG. 5 is explained in conjunction with elements from FIGS. 1, 2, 3, and 4. With reference to FIG. 5, there is shown a flowchart 500. The operations of the exemplary method may be executed by any computing system, for example, by the IV pole 102 of FIG. 1 or the circuitry 202 of FIG. 2. The operations of the flowchart 500 may start at 502 and may proceed to 514.

The method ensures that at each step, the functionalities are maintained during movement. From obtaining patient data (504) to rendering alerts (514), the system is designed to operate seamlessly whether the patient is stationary or in transit, or relocated to a new location.

At 504, the patient data associated with the patient 114 may be obtained from one or more data sources 104. In at least one embodiment, the circuitry 202 may obtain, from the one or more data sources 104, the patient data associated with the patient 114.

At 506, the one or more electronic medical health records associated with the patient 114 may be retrieved based on the obtained patient data. In at least one embodiment, the circuitry 202 may retrieve one or more electronic medical health records associated with the patient based on the obtained patient data.

At 508, the medical data associated with the patient may be retrieved from one or more medical databases 106 based on a correlation of the patient data with the one or more electronic medical health records. In at least one embodiment, the circuitry 202 may retrieve, from the one or more medical databases 106, medical data associated with the patient based on a correlation of the patient data with the one or more electronic medical health records.

At 510, the one or more AI models 108 may be applied to at least one of the patient data, the electronic medical health records, or the medical data. In at least one embodiment, the circuitry 202 may apply the one or more AI models 108 to at least one of the patient data, the electronic medical health records, or the medical data.

At 512, one or more alerts associated with a medical condition of the patient may be generated based on the application of the one or more AI models 108 to at least one of the patient data, the electronic medical health records, or the medical data. In at least one embodiment, the circuitry 202 may generate one or more alerts associated with a medical condition of the patient based on the application of the one or more AI models 108 to at least one of the patient data, the electronic medical health records, or the medical data.

At 514, the generated one or more alerts may be rendered. In at least one embodiment, the circuitry 202 may render the generated one or more alerts. Control may pass to the end.

Therefore, the disclosed multifunctional smart IV pole represents a significant advancement in medical device support systems by transforming a traditionally passive structure into an active, mobile, and integrated element of patient care. This innovation leverages technologies such as AI-driven monitoring, mesh networking, and real-time data management to enhance patient outcomes and operational efficiency within healthcare environments during and after patient relocation.

By incorporating features like location tracking, Bluetooth localization, and AI camera monitoring, the disclosed IV pole becomes a central hub for communication and monitoring, allowing for seamless integration with existing hospital systems and electronic medical records (EMRs) even during movement. This not only improves the accuracy and timeliness of patient care but also reduces the need for multiple standalone devices, leading to cost savings and streamlined operations for healthcare providers.

The potential impact of this disclosed IV pole on patient care is profound, offering enhanced safety through continuous monitoring and real-time alerts, while also supporting the digital transformation of healthcare infrastructure. In high-demand situations, such as emergency care, ICU transfers, or mass casualty events, the pole's versatile design and robust connectivity features ensure reliable performance, further demonstrating its value in improving healthcare delivery.

As the healthcare industry continues to evolve, the disclosed multifunctional smart IV pole is poised to play a pivotal role in driving innovation and efficiency, ultimately contributing to better patient outcomes and more efficient healthcare operations globally.

Figure 6:
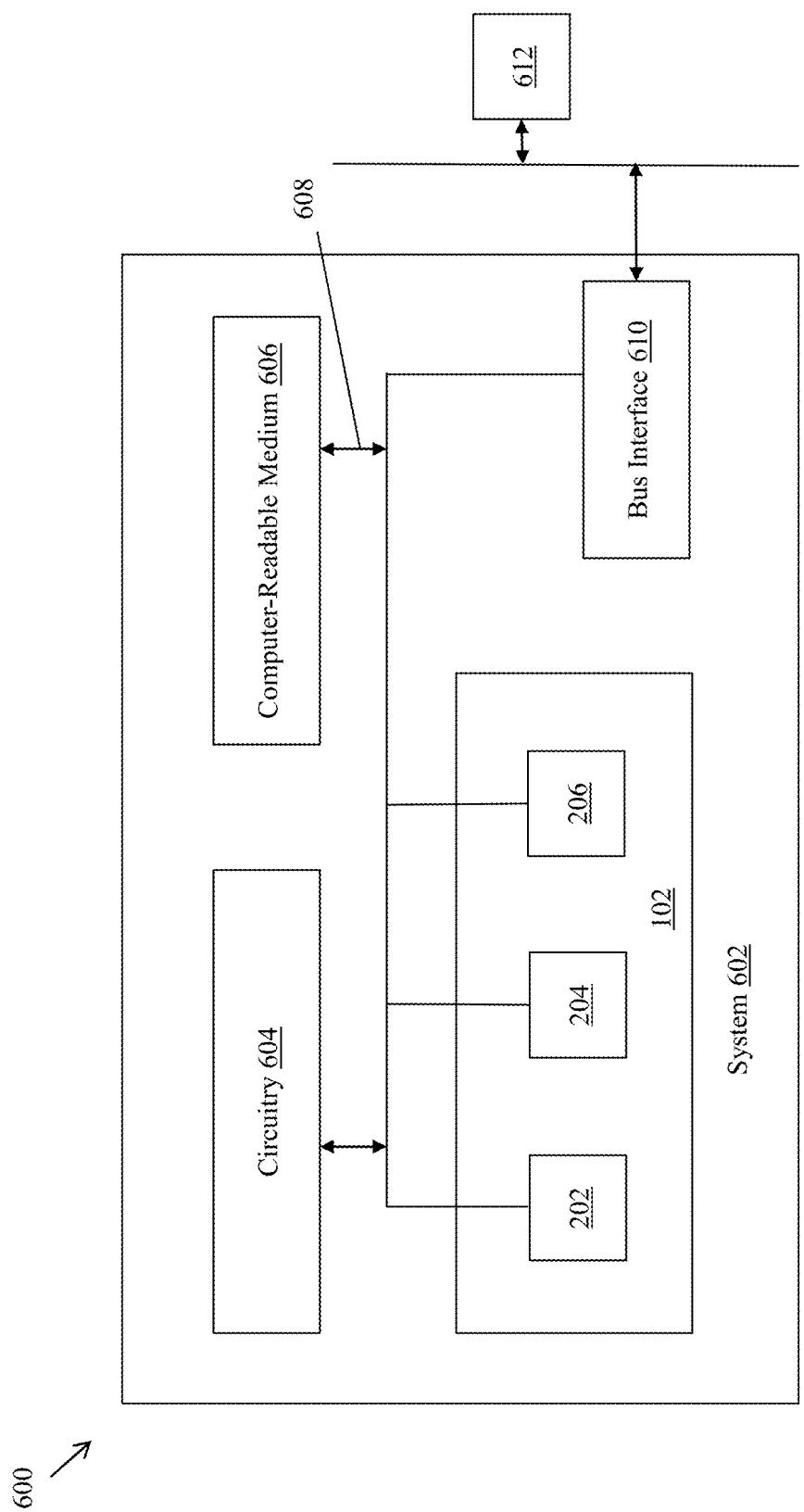
FIG. 6 is a conceptual diagram illustrating an example of a hardware implementation for the IV pole, in accordance with an exemplary embodiment of the disclosure.

FIG. 6 is a conceptual diagram illustrating an example of a hardware implementation of the IV pole, in accordance with an exemplary embodiment of the disclosure. FIG. 6 is explained in conjunction with elements from FIGS. 1, 2, 3, 4, and 5. Referring to FIG. 6, the hardware implementation shown by a representation 600 for the network environment 100 employs a processing system 602 for generation of the one or more alerts, in accordance with an exemplary embodiment of the disclosure, as described herein.

In some examples, the processing system 602 may comprise a circuitry 604, a non-transitory computer-readable medium 606, a bus 608, a bus interface 610, and a transceiver 612.

The circuitry 604, such as the circuitry 202, may be configured to manage the bus 608 and general processing, including the execution of a set of instructions stored on the non-transitory computer-readable medium 606. The set of instructions, when executed by the circuitry 604, causes the IV pole 102 to execute the various functions described herein for any particular apparatus. The circuitry 604 may be implemented, based on a number of processor technologies known in the art. Examples of the circuitry 604 may be the RISC processor, ASIC processor, CISC processor, and/or other processors or control circuits.

The non-transitory computer-readable medium 606 may be used for storing data that is manipulated by the circuitry 604 when executing the set of instructions. The data is stored for short periods or in the presence of power.

The bus 608 may be configured to link together various circuits. In this example, the network environment 100 employing the processing system 602 and the non-transitory computer-readable medium 606 may be implemented with bus architecture, represented generally by bus 608. The bus 608 may include any number of interconnecting buses and bridges depending on the specific implementation of the IV pole 102 and the overall design constraints. The bus interface 610 may be configured to provide an interface between the bus 608 and other circuits, such as the transceiver 612, and external devices, such as the display device 108A, and the server 110.

The transceiver 612 may be configured to provide a communication of the IV pole 102 with various other apparatus, such as the display device 108A, via a network. The transceiver 612 may communicate via wireless communication with networks, such as the Internet, the Intranet, and/or a wireless network, such as a cellular telephone network, a wireless local area network (WLAN), and/or a metropolitan area network (MAN). The wireless communication may use any of a plurality of communication standards, protocols and technologies, such as 5th generation mobile network, Global System for Mobile Communications (GSM), Enhanced Data GSM Environment (EDGE), Long Term Evolution (LTE), wideband code division multiple access (W-CDMA), code division multiple access (CDMA), time division multiple access (TDMA), Bluetooth, Wireless Fidelity (Wi-Fi) (such as IEEE 802.11a, IEEE 802.11b, IEEE 802.11g and/or IEEE 802.11n), voice over Internet Protocol (VOIP), and/or Wi-MAX.

It should be recognized that, in some embodiments of the disclosure, one or more components of FIG. 6 may include software whose corresponding code may be executed by at least one processor, for across multiple processing environments.

In an aspect of the disclosure, the circuitry 604, the non-transitory computer-readable medium 606, or a combination of both may be configured or otherwise specially programmed to execute the operations or functionality of the circuitry 202, the memory 204, the I/O device 206, the network interface 208, and the one or more AI models 108 or various other components described herein, as described with respect to FIGS. 1 to 6.

As utilized herein, the term "exemplary" means serving as a non-limiting example, instance, or illustration. As utilized herein, the terms "for example," and "for example" set off lists of one or more non-limiting examples, instances, or illustrations. As utilized herein, circuitry is "operable" to perform a function whenever the circuitry comprises the necessary hardware and/or code (if any is necessary) to perform the function, regardless of whether the performance of the function is disabled, or not enabled, by some user-configurable setting.

The terminology used herein is for the purpose of describing particular embodiments only and is not intended to be limiting of embodiments of the disclosure. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Further, many embodiments are described in terms of sequences of actions to be performed by, for example, elements of a computing device. It will be recognized that various actions described herein can be performed by specific circuits (for example, application specific integrated circuits (ASICs)), by program instructions being executed by one or more processors, or by a combination of both. Additionally, these sequences of actions described herein can be considered to be embodied entirely within any non-transitory form of computer readable storage medium having stored therein a corresponding set of computer instructions that upon execution would cause an associated processor to perform the functionality described herein. Thus, the various aspects of the disclosure may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Another embodiment of the disclosure may provide a non-transitory machine and/or computer-readable storage and/or media, having stored thereon, a machine code and/or a computer program having at least one code section executable by a machine and/or a computer, thereby causing the machine and/or computer to perform the steps as described herein for generating a novel molecular structure using a protein structure.

The present disclosure may also be embedded in a computer program product, which comprises all the features enabling the implementation of the methods described herein, and which when loaded in a computer system is able to carry out these methods. Computer program in the present context means any expression, in any language, code or notation, either statically or dynamically defined, of a set of instructions intended to cause a system having an information processing capability to perform a particular function either directly or after either or both of the following: a) conversion to another language, code or notation; b) reproduction in a different material form.

Further, those of skill in the art will appreciate that the various illustrative logical blocks, modules, circuits, algorithms, and/or steps described in connection with the embodiments disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The methods, sequences and/or algorithms described in connection with the embodiments disclosed herein may be embodied directly in firmware, hardware, in a software module executed by a processor, or in a combination thereof. A software module may reside in RAM memory, flash memory, ROM memory, EPROM memory, EEPROM memory, registers, hard disk, physical and/or virtual disk, a removable disk, a CD-ROM, virtualized system or device such as a virtual server or container, or any other form of storage medium known in the art. An exemplary storage medium is communicatively coupled to the processor (including logic/code executing in the processor) such that the processor can read information from, and write information to, the storage medium. In the alternative, the storage medium may be integral to the processor.

While the present disclosure has been described with reference to certain embodiments, it will be noted understood by, for example, those skilled in the art that various changes and modifications could be made and equivalents may be substituted without departing from the scope of the present disclosure as defined, for example, in the appended claims. In addition, many modifications may be made to adapt a particular situation or material to the teachings of the present disclosure without departing from its scope. The functions, steps and/or actions of the method claims in accordance with the embodiments of the disclosure described herein need not be performed in any particular order. Furthermore, although elements of the disclosure may be described or claimed in the singular, the plural is contemplated unless limitation to the singular is explicitly stated. Therefore, it is intended that the present disclosure is not limited to the particular embodiment disclosed, but that the present disclosure will include all embodiments falling within the scope of the appended claims.

What is claimed is:

1. An intravenous (IV) pole, comprising:
   at least one antenna configured to maintain uninterrupted data connectivity;
   a network interface; and
   a circuitry configured to:
      obtain, from one or more real-time physiological sensors and medical monitoring devices, patient data associated with a patient;
      retrieve one or more electronic medical health records associated with the patient based on the obtained patient data;
      retrieve, from one or more medical databases, medical data associated with the patient based on a correlation of the patient data with the one or more electronic medical health records;
      apply one or more artificial intelligence (AI) models to at least one of the patient data, the electronic medical health records, or the medical data, wherein the AI models process real-time physiological data continuously, including during patient movement;
      generate one or more alerts associated with a medical condition of the patient based on the application of the one or more AI models, wherein the alerts are dynamically updated based on real-time changes in patient status; and
      render the generated one or more alerts on a display device communicatively linked to the IV pole.

2. The IV pole according to claim 1, wherein the one or more real-time physiological sensors and medical monitoring devices comprises at least one of: a set of diagnostic medical devices associated with the patient, a set of monitoring devices associated with the patient, a set of scanning devices associated with the patient, a set of wearable devices associated with the patient, a set of fluid administration devices associated with the patient, and a set of sensors, and wherein the one or more data sources are associated with the IV pole.

3. The IV pole according to claim 1, wherein the circuitry is further configured to:
   encrypt the patient data, the one or more electronic medical health records, or the one or more alerts, wherein the one or more electronic medical health records, or the one or more alerts are encrypted using one or more encryption techniques; and
   transmit, via the network interface, the encrypted patient data, the encrypted one or more electronic medical health records, or the encrypted one or more alerts to at least one electronic device of a set of electronic devices.

4. The IV pole according to claim 3, wherein the circuitry is further configured to:
   receive a set of instructions associated with an administration of one or more fluids to the patient based on the transmission; and
   control a flow rate of the one or more fluids to the patient based on the received set of instructions.

5. The IV pole according to claim 3, wherein the one or more encryption techniques comprise at least one of: an Advanced Encryption Standard (AES) technique, a Data Encryption Standard (DES) technique, a Triple Data Encryption Standard (3DES) technique, a Rivest-Shamir-Adleman (RSA) technique, an Elliptic Curve Cryptography (ECC) technique, and a Blowfish (BF) technique.

6. The IV pole according to claim 1, wherein the circuitry is further configured to:
 obtain location data associated with a location of at least one user device of a set of user devices associated with a set of medical professionals;
 generate a set of navigation instructions based on the obtained location data; and
 transmit the generated navigation instructions to the at least one user device of the set of user devices.

7. The IV pole according to claim 1, further comprising an image capture sensor, and wherein the circuitry is further configured to:
 control the image capture sensor to capture an image of a wound of the patient, wherein the patient data comprises of the captured image;
 apply a first AI model of the one or more AI models on the captured image; and
 generate the one or more alerts associated with the medical condition of the patient based on the application of the first AI model on the captured image.

8. The IV pole according to claim 1, wherein the circuitry is further configured to:
 obtain, from the one or more data sources, the patient data associated with the patient, wherein the one or more data sources comprises at least one of a set of wearable devices associated with the patient, and a set of sensors;
 apply a second AI model of the one or more AI models on the obtained patient data, wherein the patient data comprises at least one of accelerometer data associated with a movement of the patient, or gyroscopic data associated with the movement of the patient; and
 generate the one or more alerts associated with the medical condition of the patient based on the application of the second AI model on the obtained patient data, monitoring patient stability during at least one the movement of the IV pole or during the relocation of the patient.

9. The IV pole according to claim 8, wherein the circuitry is further configured to:
 apply a third AI model of the one or more AI models on the obtained patient data; and
 generate the one or more alerts associated with the medical condition of the patient based on the application of the third AI model on the obtained patient data, wherein the one or more alerts are indicative of a repositioning of the patient to prevent one or more pressure sores associated with the patient, even during at least one the movement of the IV pole or during the relocation of the patient.

10. The IV pole according to claim 1, wherein the IV pole is connected with one or more display devices using a customized active cable arrangement designed to maintain connectivity during at least one the movement of the IV pole or during the relocation of the patient.

11. The IV pole according to claim 1, wherein the circuitry is further configured to:
 receive a first user input associated with retraction of the at least one antenna; and
 control the at least one antenna to retract inside the IV pole based on the received first user input.

12. The IV pole according to claim 1, further comprising a set of visual indicators, wherein the circuitry is further configured to:
 control a display of a first color in a first visual indicator of the set of visual indicators based on the patient data.

13. An intravenous (IV) pole system, comprising:
 a network interface configured to communicate with external hospital or clinical information systems;
 one or more connection interfaces configured to connect with a plurality of medical devices or equipment;
 a data acquisition module configured to receive real-time physiologic and device data from the connected medical devices or equipment;
 a processing unit configured to apply one or more artificial intelligence (AI) models to the received physiologic and device data, wherein the AI models process real-time physiologic and device data continuously, including during patient movement; and
 an integrated antenna configured to support wireless transmission and reception of data.

14. The system of claim 13, further comprising a rechargeable battery configured to supply power to the system during transport or mobile use.

15. The system of claim 13, wherein the IV pole comprises a power management module configured to monitor battery charge status and provide visual alerts when battery life is below a threshold.

16. The system of claim 13, further comprising a retractable or collapsible antenna integrated into the IV pole housing.

17. The system of claim 13, wherein the IV pole is configured to connect to a plurality of bedside medical devices including, but not limited to: patient monitors, infusion pumps, ventilators, dialysis machines, and ECG machines.

18. The system of claim 13, further comprising a user interface or display panel configured to show device connection status, system diagnostics, or patient-assigned identifiers.

19. The system of claim 13, wherein the network interface supports wireless communication protocols including at least one of: WiFi, Bluetooth, LoRa, or 5G.

20. A non-transitory computer-readable medium including computer program instructions, which when executed by an intravenous (IV) pole comprising at least one antenna, and a network interface, cause the IV pole to perform one or more operations comprising:
 obtaining, from one or more real-time physiological sensors and medical monitoring devices, patient data associated with a patient;
 retrieving one or more electronic medical health records associated with the patient based on the obtained patient data;
 retrieving, from one or more medical databases, medical data associated with the patient based on a correlation of the patient data with the one or more electronic medical health records;
 applying one or more artificial intelligence (AI) models to process real-time physiological data continuously, including during patient movement;
 generating one or more alerts associated with a medical condition of the patient based on the application of the one or more AI models to dynamically update the one or more alerts based on real-time changes in patient status; and rendering the generated one or more alerts on a display device communicatively linked to the IV pole.

* * * * *